US008361808B2

(12) United States Patent
Wang

(10) Patent No.: US 8,361,808 B2
(45) Date of Patent: Jan. 29, 2013

(54) CAPILLARY FLOW SOLID PHASE ASSAY

(75) Inventor: Dequn Wang, San Diego, CA (US)

(73) Assignee: Oranoxis, Inc., San Diego, CA (US)

(*) Notice: Subject to any disclaimer, the term of this patent is extended or adjusted under 35 U.S.C. 154(b) by 265 days.

(21) Appl. No.: 12/650,393

(22) Filed: Dec. 30, 2009

(65) Prior Publication Data

US 2010/0167419 A1    Jul. 1, 2010

Related U.S. Application Data

(60) Provisional application No. 61/203,924, filed on Dec. 31, 2008.

(51) Int. Cl.
*G01N 33/558* (2006.01)
(52) U.S. Cl. ............ 436/514; 422/411; 435/970; 435/4; 435/6.19; 435/7.1; 435/287.1; 435/287.2; 435/287.3; 435/287.7; 435/287.8; 435/287.9; 435/288.3; 435/288.4; 435/288.5; 436/501; 436/518; 436/535; 436/536; 436/538; 436/540; 604/1
(58) Field of Classification Search ............... 422/411; 435/970, 4, 6.19, 7.1, 7.5, 7.9, 7.92–7.95, 435/286.1, 286.2, 286.5, 287.1–287.3, 287.7, 435/287.8, 287.9, 288.3, 288.4, 288.5; 436/501, 436/514, 518, 535, 536, 538, 540, 541, 543, 436/544, 546; 600/582, 365; 604/1
See application file for complete search history.

(56) References Cited

U.S. PATENT DOCUMENTS

| 6,890,484 | B2 * | 5/2005 | Bautista et al. ............... 422/412 |
| 7,090,803 | B1 * | 8/2006 | Gould et al. .................. 422/413 |
| 2004/0184954 | A1 * | 9/2004 | Guo et al. ........................ 422/56 |

OTHER PUBLICATIONS

International Search Report and Written mailed on Sep. 2, 2010, for PCT/US2009/069872, international filing date Dec. 30, 2009 (10 pp).

* cited by examiner

*Primary Examiner* — Melanie J Yu
*Assistant Examiner* — Erik B Crawford
(74) *Attorney, Agent, or Firm* — Perkins Coie LLP

(57) ABSTRACT

Methods, materials, apparatus and systems are described for performing capillary flow assay. In one aspect, a system includes a sample collection unit to collect a sample liquid and a sample testing and storing unit to interface with the sample collection unit to test and store the collected sample liquid. The sample testing and storing unit includes a sample inlet shaped to receive the collected sample from the sample collection unit, and a sample well positioned below the sample inlet to retain at least a portion of the sample liquid. The sample testing and storing unit includes a sample housing unit to store a remainder of the sample liquid not retained in the sample well, and an analyte testing unit housing shaped to receive an analyte detecting unit to test a presence of a target analyte in the sample liquid.

10 Claims, 20 Drawing Sheets

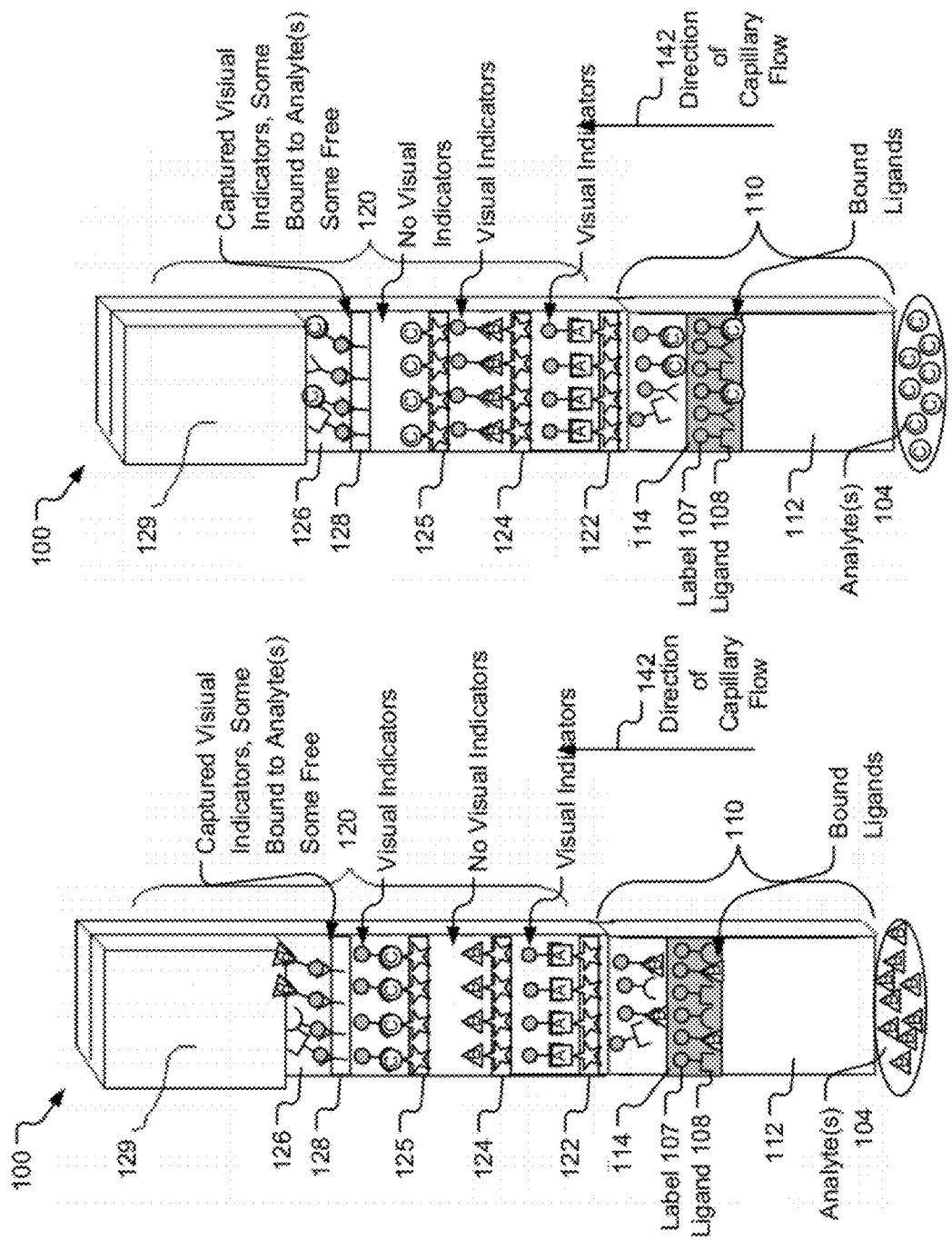

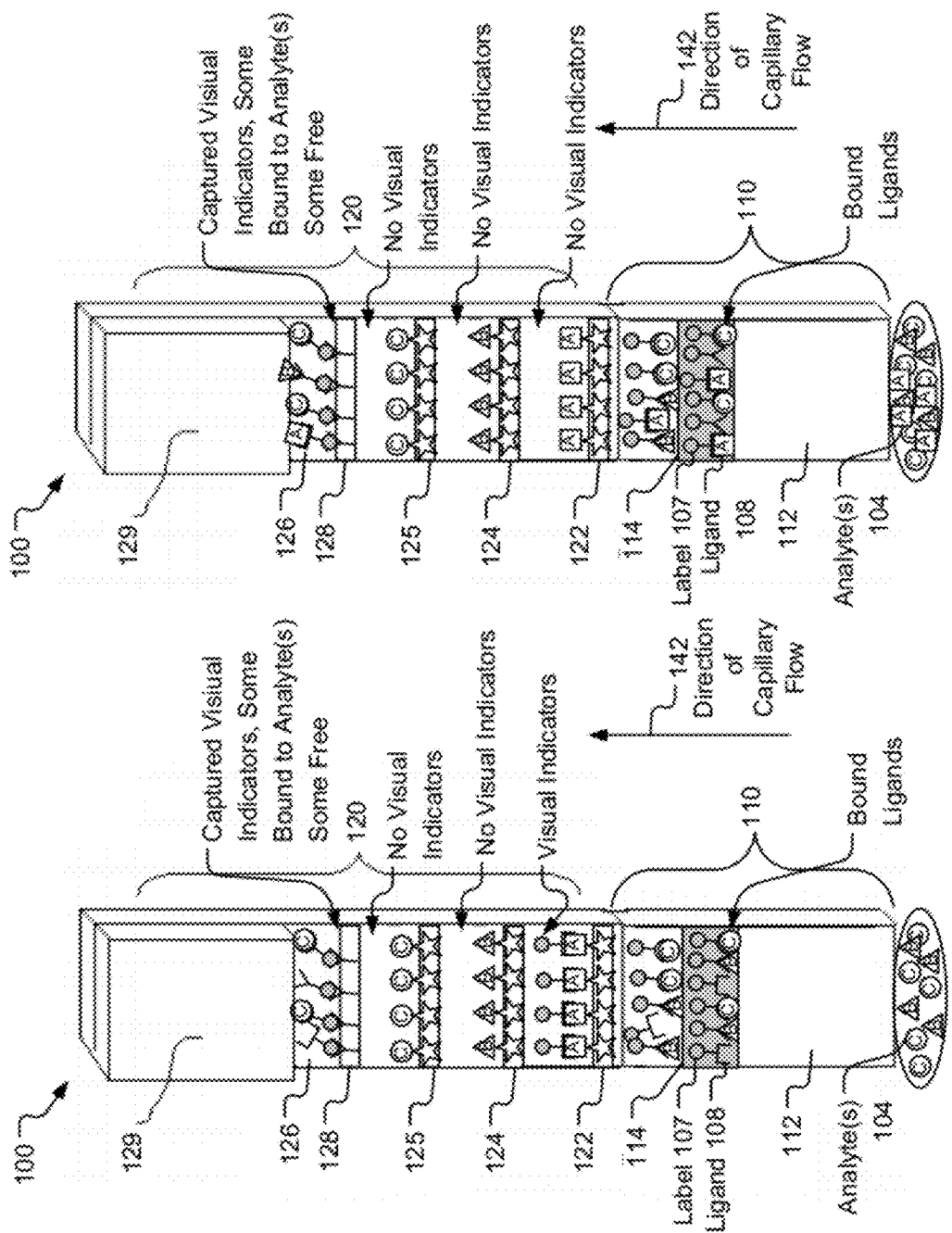

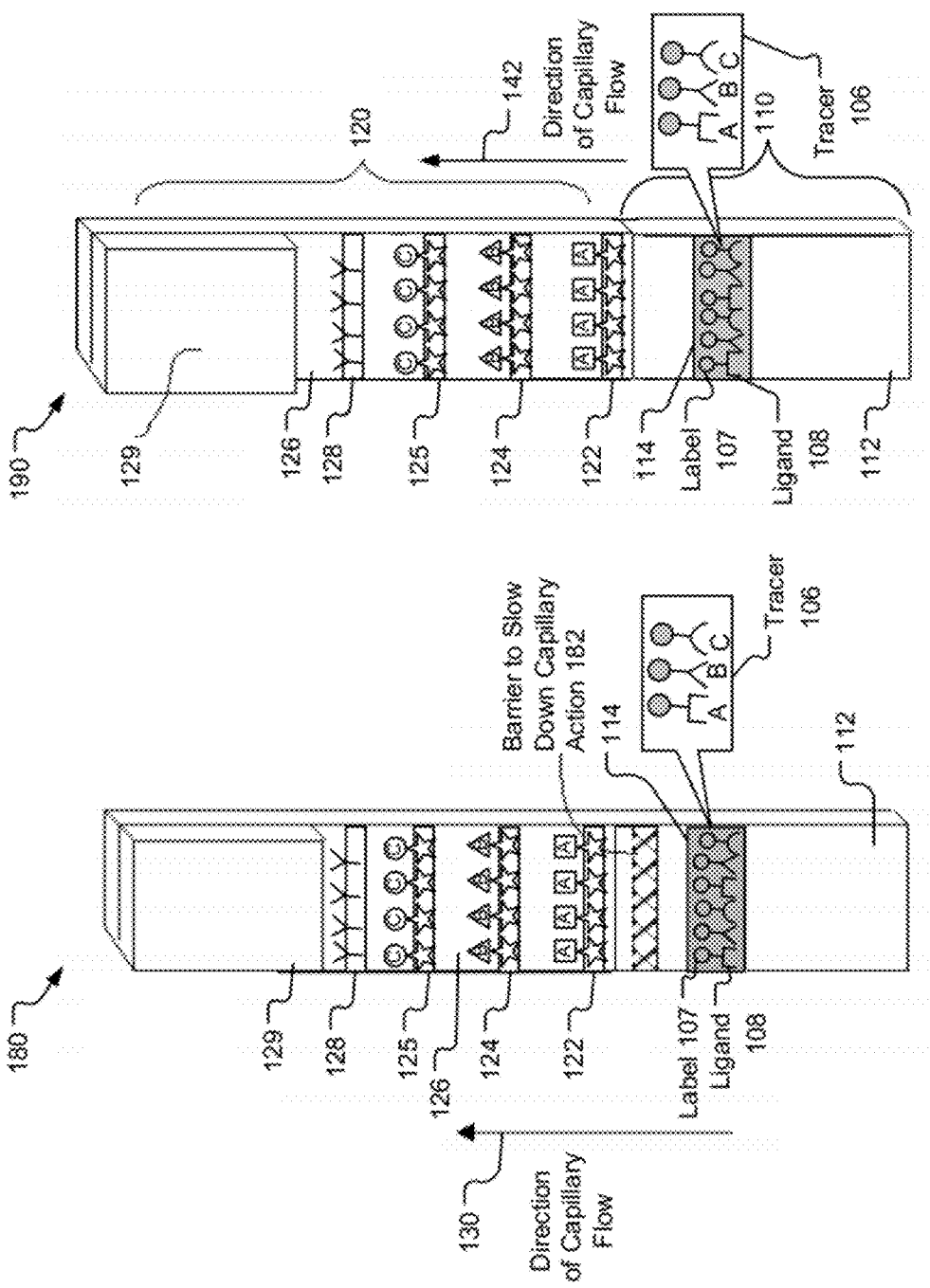

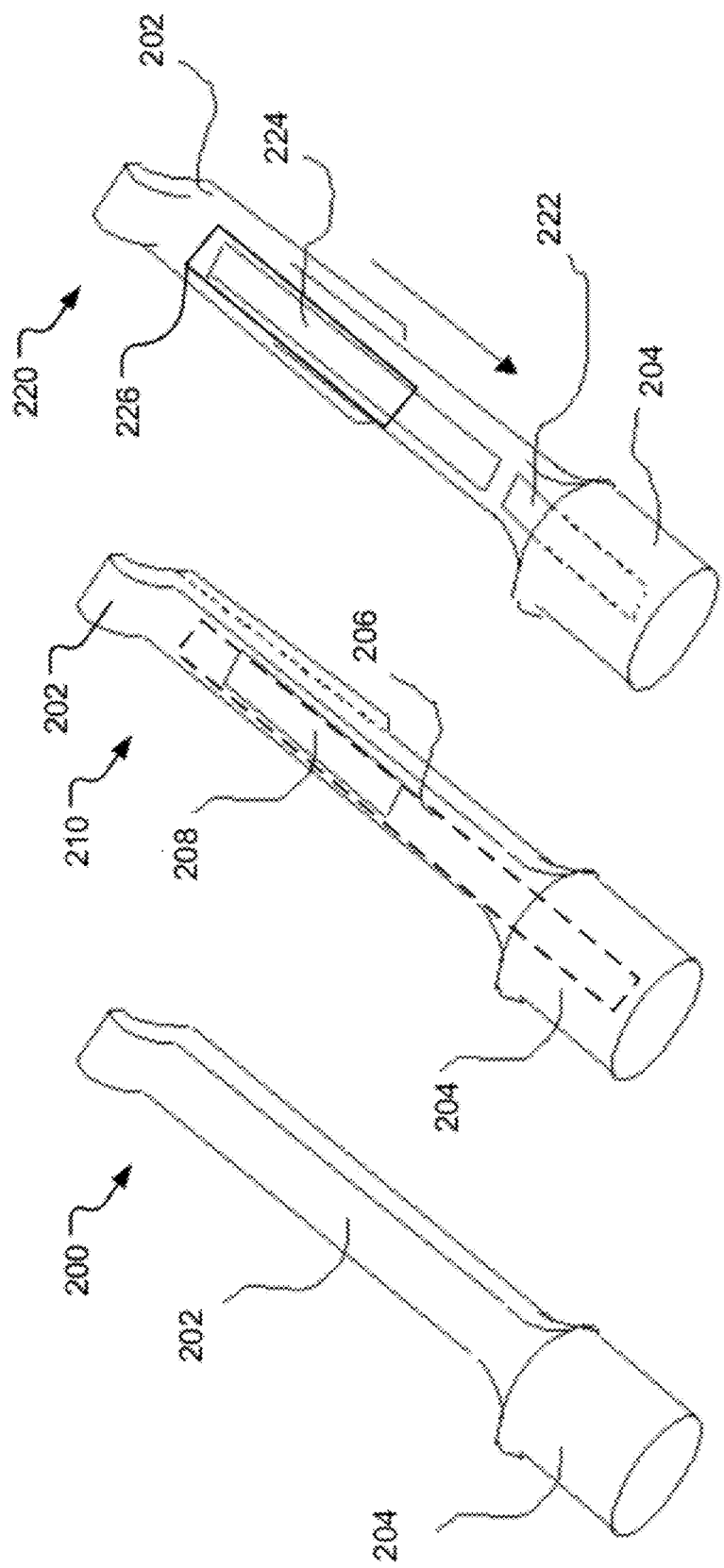

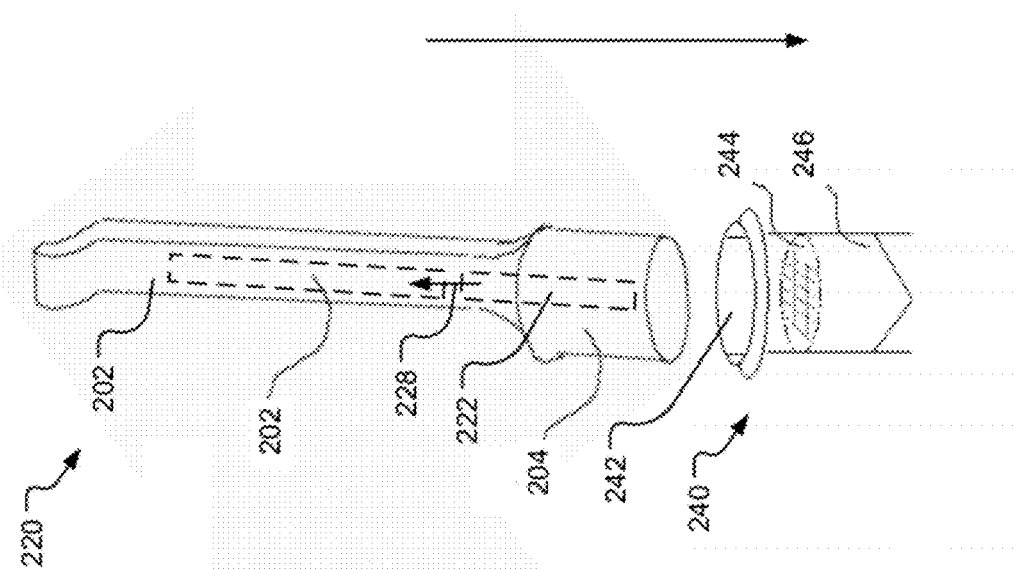
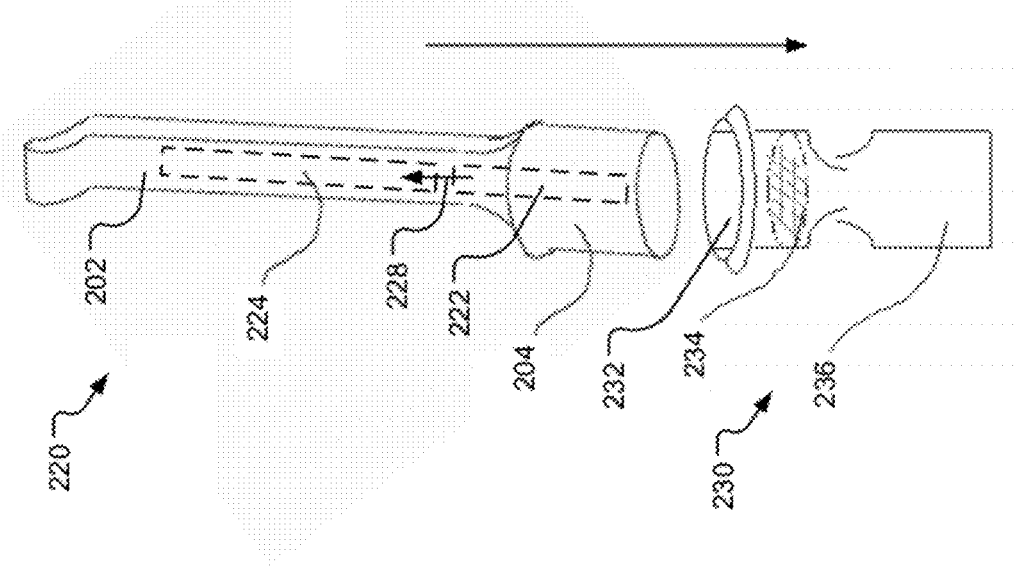

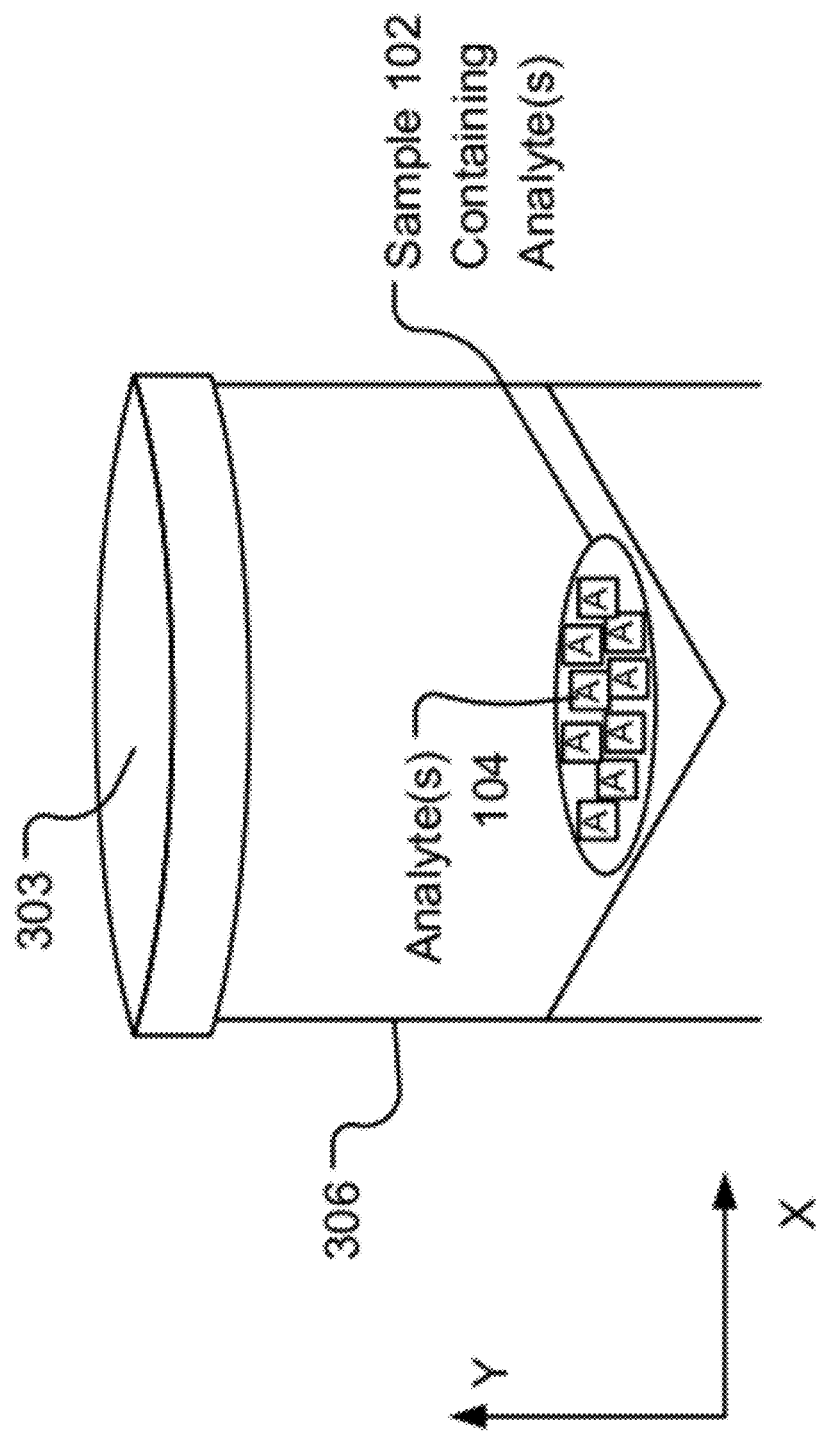

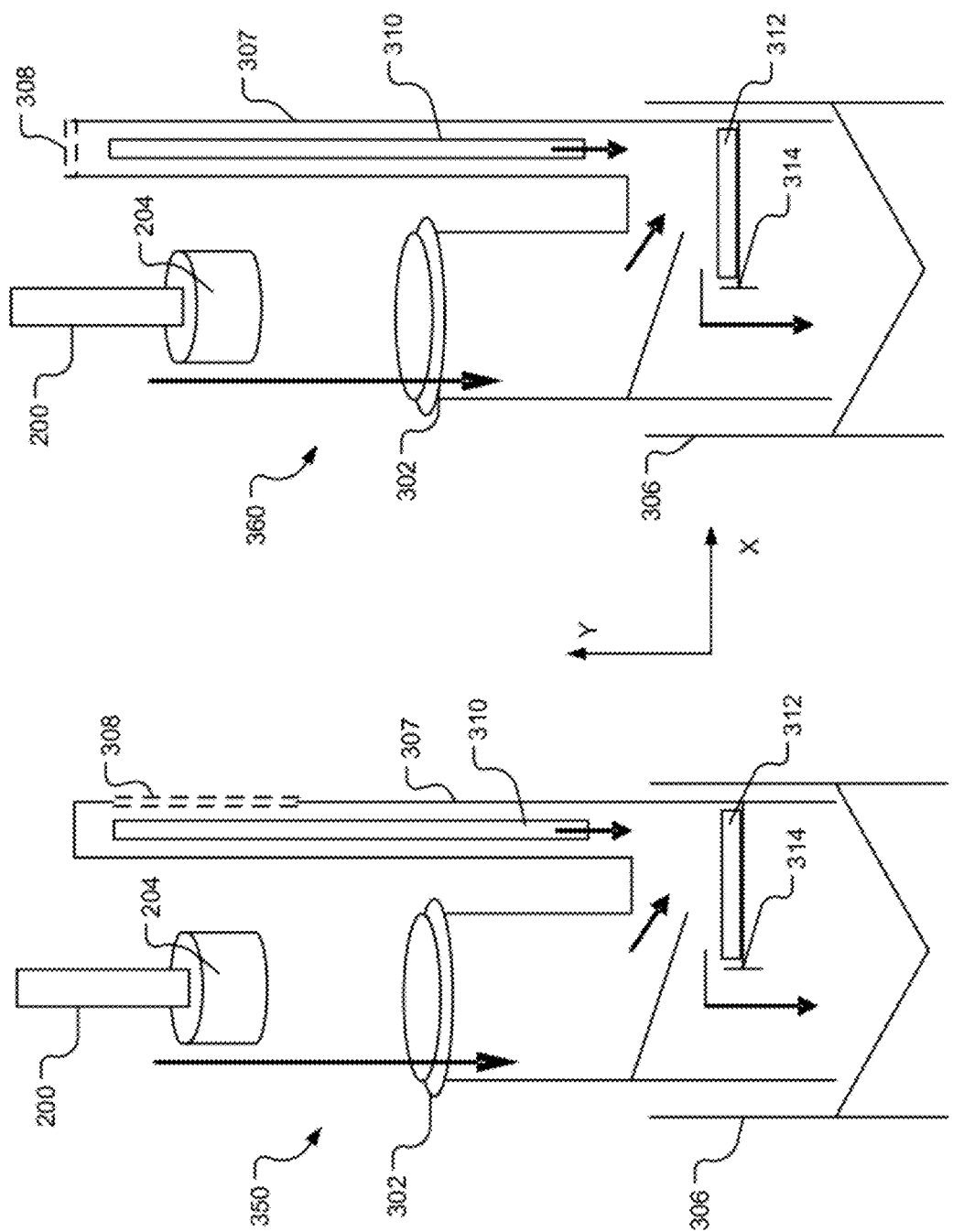

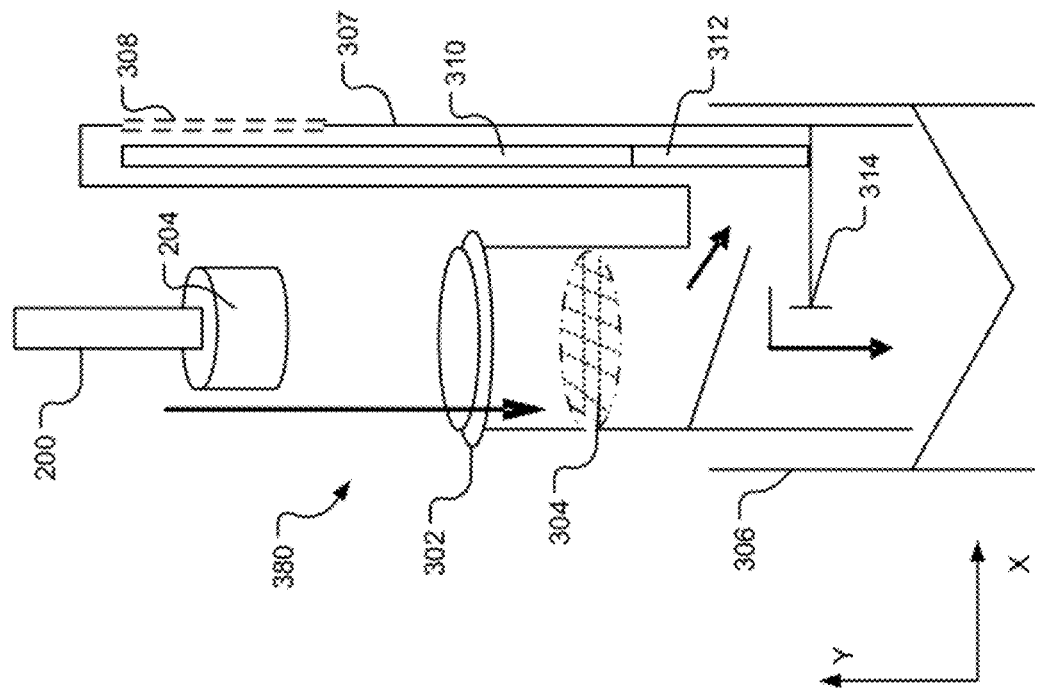
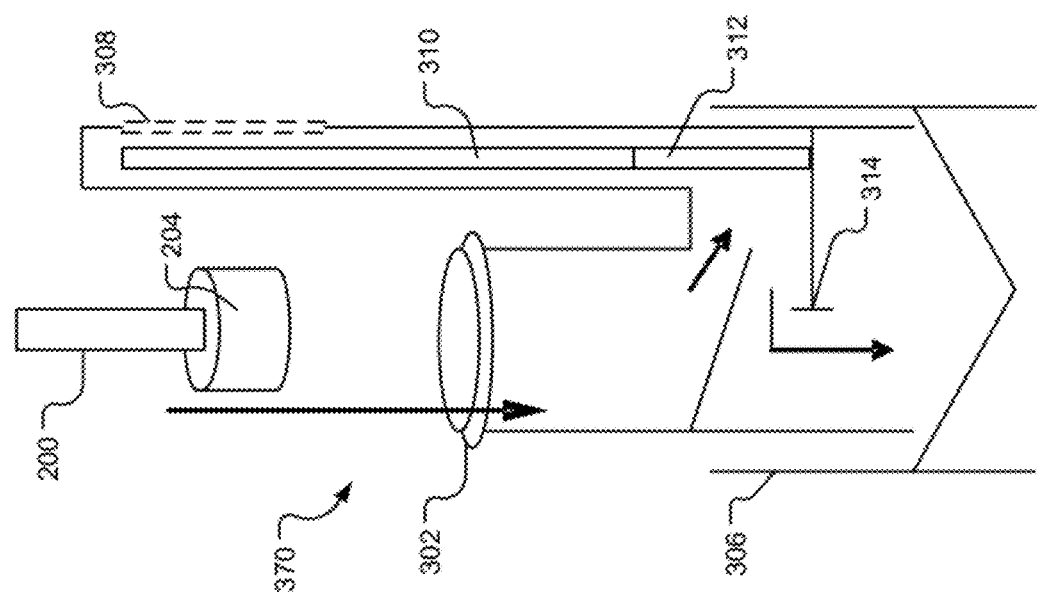

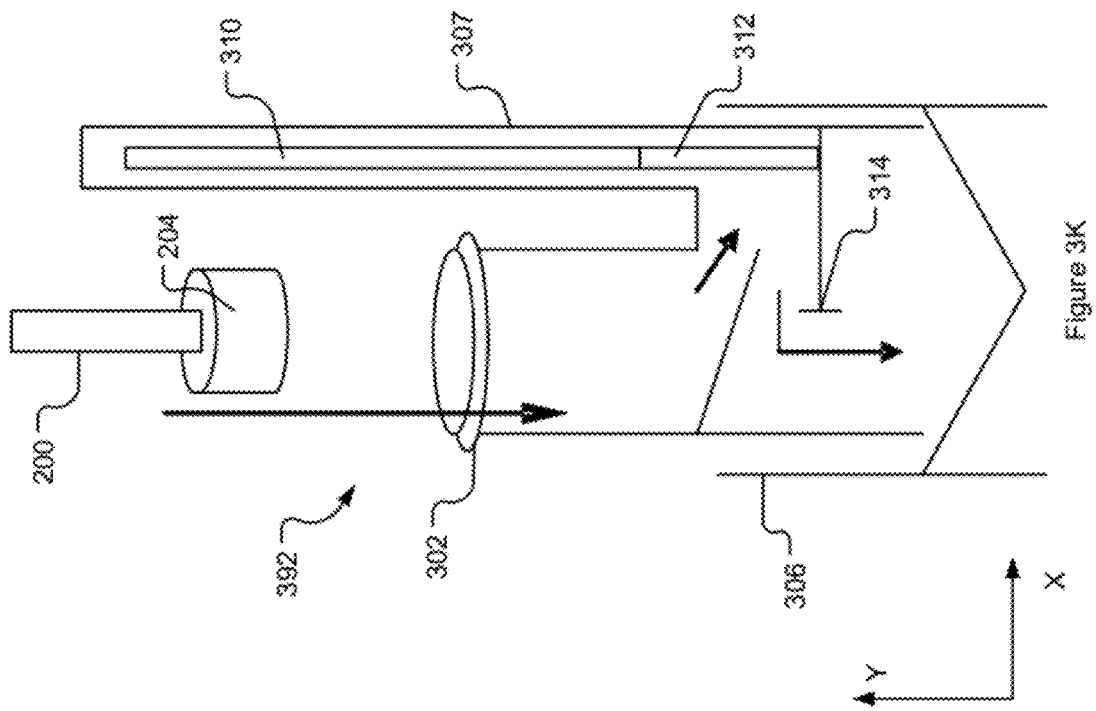
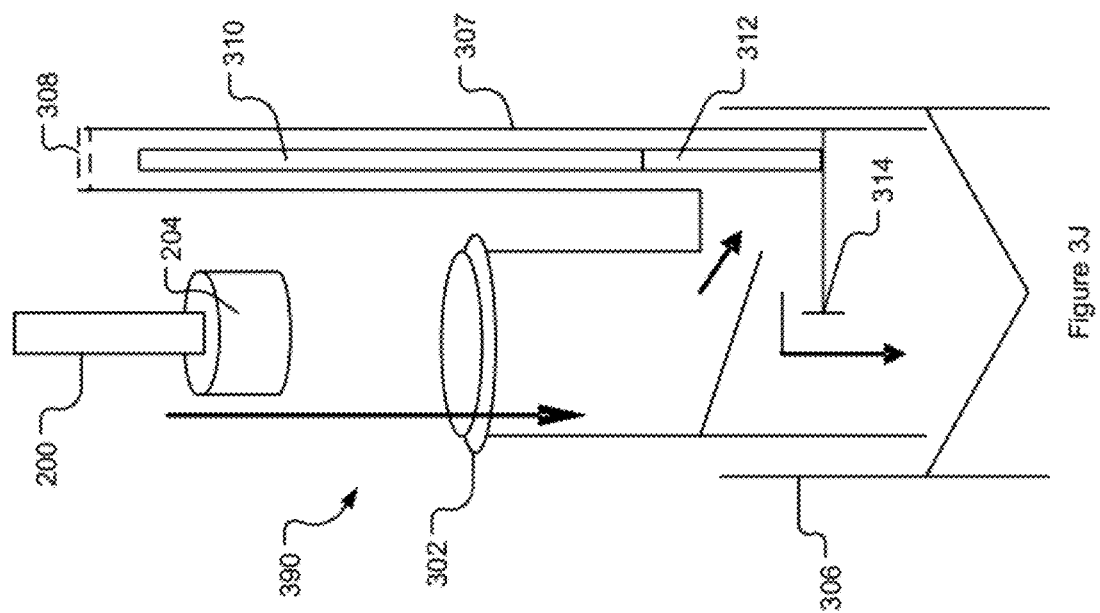

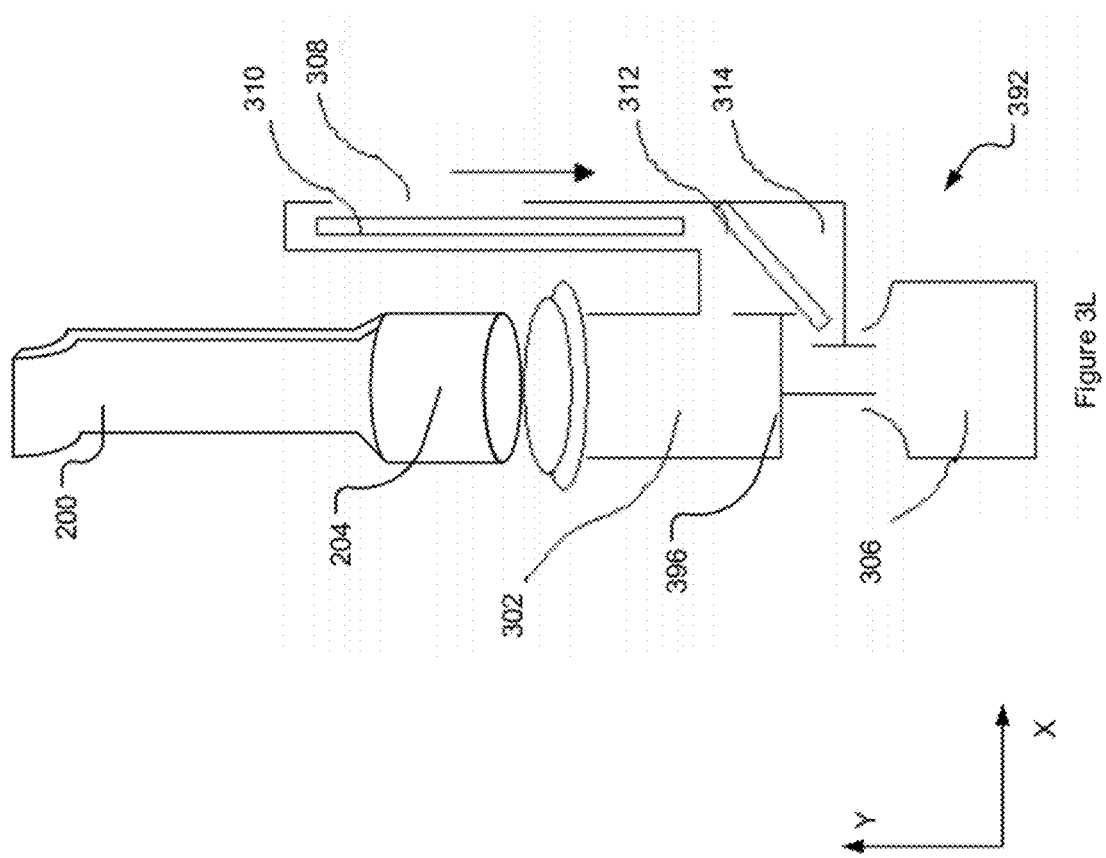

CAPILLARY FLOW SOLID PHASE ASSAY

CLAIM OF PRIORITY

This application claims priority under 35 USC §119(e) to U.S. Patent Application Ser. No. 61/203,924, filed on Dec. 31, 2008, the entire contents of which are hereby incorporated by reference.

BACKGROUND

This application relates to capillary flow assays.

Various lateral flow assay techniques can be used to determine the presence or absence of analytes in a sample. For example, lateral flow assay can be used to detect the presence of drugs in bodily fluids such as blood, urine, saliva and other liquid samples. A lateral flow assay device includes a single continuous solid piece of absorbent material that allows analytes to move from one end of the material to the other end once a sample containing the analytes is in contact with the one end of the material.

SUMMARY

Techniques, systems and apparatus are disclosed for implementing a capillary flow assay device that can detect a presence of target analytes in a sample. Additionally, a collection unit can be implemented with the capillary flow assay device to collect and retain the sample to confirm the assay findings.

In one aspect, a system for performing lateral capillary flow assay includes a sample collection unit to collect a sample liquid; and a sample testing and storing unit to interface with the sample collection unit to test and store the collected sample liquid. The sample testing and storing unit includes a sample inlet shaped to receive the collected sample from the sample collection unit. The sample testing and storing unit includes a sample well positioned below the sample inlet to retain at least a portion of the sample liquid. The sample testing and storing unit includes a sample housing unit to store a remainder of the sample liquid not retained in the sample well. The sample testing and storing unit includes an analyte testing unit housing shaped to receive an analyte testing unit to test a presence of a target analyte in the sample liquid. The analyte testing unit includes a sample receiving area to receive the sample liquid. The analyte testing unit includes an indicator holding area to temporarily hold at least one type of indicator material that binds with a corresponding target analyte in the sample liquid to form an analyte-indicator complex that flows across the analyte testing unit under capillary action. The analyte testing unit includes at least one binding area to immobilize at least one type of binder material configured to bind with the at least one type of indicator material, at least one analyte, or both the at least one analyte and the at least one type of indicator material. A presence of the corresponding type of indicator material at the at least one binding area indicates an absence of a corresponding type of target analyte. The analyte testing unit includes a validation area that includes a ligand or a binder material that selectively binds to the at least one type of indicator material to confirm that the at least one type of indicator material properly flowed across the analyte testing unit under capillary action.

Implementations can optionally include one or more of the following features. The analyte testing unit can include a single test strip with at least a portion of the single test strip that includes the sample receiving area positioned within the sample well to receive the sample liquid in the sample well. The analyte testing unit housing can include an analyte testing unit inlet positioned above the sample well to allow the single test strip to drop towards the sample well by gravity and in physical contact with the sample liquid in the sample well. The analyte testing unit can include the sample receiving area and the indicator holding area, and at least one binding area and the validation area. an absorbent material positioned at the end of the strip to hold the liquid that has flew through the binding areas and validation area on the membrane.

The analyte testing unit can include multiple structures that includes a first structure that includes the sample receiving area and the indicator holding area, and a second structure that is physically separated from the first structure. The second structure can include the at least one binding area and the validation area. The second structure can include an absorbent material positioned at the end of the strip to hold the liquid that has flew through the binding areas and validation area on the membrane The analyte testing unit housing can include an analyte testing unit inlet positioned above the sample well to allow the second structure of the analyte testing unit to drop towards the sample well by gravity and in physical contact with the first structure of the analyte testing unit. The indicator material can include a ligand and a label that can be visualized based on color or measured for fluorescent, magnetic, chemiluminescent and colormetric signals. The label can include an agent selected from a group comprising a gold colloid, latex nanoparticles, iron nanoparticles, an enzyme, a fluorescent material, and a chemiluminescent material. The label can be directly or indirectly linked to the ligand. The ligand can include a chemical substance that selectively binds with the at least one analyte, the binder material or both the at least one analyte and the binder material. The at least one analyte can include a chemical substance that selectively binds with the ligand, the binder material or both the ligand and the binder material. The binder material can include a chemical substance that selectively binds with the ligand, the indicator material or both the ligand and the indicator material. A filtering unit can be attached to an inner surface of the sample inlet to filter the sample liquid received from the sample collection unit.

In another aspect, a device for assaying a sample can include an analyte testing unit to test a presence of a target analyte in a sample liquid. The testing unit includes a sample receiving structure. The sample receiving structure includes a sample receiving area that includes an absorbent material to receive the sample liquid; and an indicator holding area to temporarily hold at least one type of indicator material that binds with a corresponding target analyte in the sample liquid to form an analyte-indicator complex that flows across the analyte testing unit under capillary action. The testing unit includes a sample testing structure. The sample testing structure includes at least one binding area to immobilize at least one type of binder material configured to bind with the at least one type of indicator material, at least one analyte, or both the at least one analyte and the at least one type of indicator material. A presence of the corresponding type of indicator material at the at least one binding area indicates an absence of a corresponding type of target analyte. The sample testing structure includes a validation area comprising a ligand or a binder material that selectively binds to the at least one type of indicator material to confirm that the at least one type of indicator material properly flowed across the analyte testing unit under capillary action.

Implementations can optionally include one or more following features. The sample receiving structure can include a first test strip; and the sample testing structure can include a second test strip physically separate from the first test strip. In some implementations, the analyte testing unit can include a single unit that integrates the sample receiving unit and the sample testing unit. The device can include a barrier unit positioned between the sample receiving structure and the sample testing structure to temporarily maintain the sample receiving structure and the sample testing structure physically separate. The barrier can include a material to slow down capillary flow from the first test strip across to the second test strip.

A method of performing capillary flow assay includes obtaining a sample liquid. The method includes contacting the obtained sample liquid with a first test strip that includes an indicator holding area to temporarily hold at least one type of indicator material that binds with a corresponding analyte present in the sample liquid and form an analyte-indicator complex that flows across the first test strip under capillary action. The method includes maintaining the contact between the obtained sample liquid and the first test strip for a predetermined time period to allow the at least one type of indicator material on the first test strip to bind with the corresponding target analyte present in the sample liquid. The method includes contacting a second test strip, physically separate from the first test strip, with the first test strip, wherein the second test strip includes at least one binding area to immobilize at least one binder material configured to bind with the at least one type of indicator material, at least one analyte, or both the at least one analyte and the at least one type of indicator material. The method includes detecting a presence of at least one target analyte based on a location of the at least one type of indicator material, the analyte-indicator complex, or both the at last one type of indicator material and the analyte-indicator complex on the second test strip.

Implementations can optionally include one or more of the following features. The predetermined time period can include a time period in the range of 10 seconds to 10 hours. In some implementations, the predetermined time period can include a time period in the range of 10 seconds to 10 minutes.

The subject matter described in this specification potentially can provide one or more of the following advantages. The described techniques, apparatus and systems can be used to implement a continuous or discontinuous capillary flow assay device that can temporarily discontinue the capillary flow to provide a sustained incubation time for any analytes in the sample to bind to the ligands disposed in the essay device. The discontinuous capillary flow assay device can be configured to allow the user to control the incubation time. By allowing the user to control the incubation time, the assay test sensitivity can be improved. Additionally, a collection unit can be provided with the continuous or discontinuous capillary flow assay device to collect and retain the sample for further testing to confirm the assay results. The described techniques, apparatus and system can improve assay sensitivity by increasing the contact between the analyte and the tracer material before both reach the binder material in a capillary flow device.

BRIEF DESCRIPTION OF THE DRAWINGS

FIG. 1E shows an example of detecting type B analytes in a sample liquid.

FIG. 1F shows an example of detecting type C analytes in a sample liquid.

FIG. 1G shows an example of detecting a combination of different analyte types (e.g., type B and type C) in a sample liquid).

FIG. 1H shows an example of detecting all of the different types present in a sample liquid.

FIG. 1I shows another example of a discontinuous capillary flow device that includes a barrier layer.

FIG. 1J shows an example of an integrated capillary flow device comprising a single unit.

FIG. 2A shows a sample collection unit that includes a handle and a collection mechanism.

FIG. 2B shows a sample collection unit that contains an assay device (e.g., test strip).

FIG. 2C shows a sample collection unit that contains an assay device (e.g., test strip) implemented as two separate pieces.

FIG. 2D shows a sample retaining devices that can interact with a sample collection device to receive and retain a sample.

FIG. 2E shows another sample retaining devices that can interact with a sample collection device to receive and retain a sample.

FIG. 3B shows an example of a sample retaining unit with a cap separated from rest of a capillary flow assay device.

FIG. 3F shows yet another design or implementation of a capillary flow assay device or system without a filtering unit.

FIG. 3G shows yet another example of a capillary flow assay device or system without a filtering unit is made optional and a testing unit inlet placed at a top surface of a testing unit housing unit.

FIG. 3H shows an example of a capillary flow assay device or system that uses a testing unit that integrates a first piece and a second piece as a single unit.

FIG. 3I shows another design or implementation of a capillary flow assay device or system that uses a single unit testing unit.

FIG. 3J shows yet another design or implementation of a capillary flow assay device that uses a single unit testing unit.

FIG. 3K shows yet another design or implementation or implementation of a capillary flow assay device or system that uses a single unit testing unit.

FIG. 3L shows an example wherein a sample retaining unit is shaped differently (e.g., having a flat bottom).

Like reference symbols and designations in the various drawings indicate like elements.

DETAILED DESCRIPTION

Figure 1A:
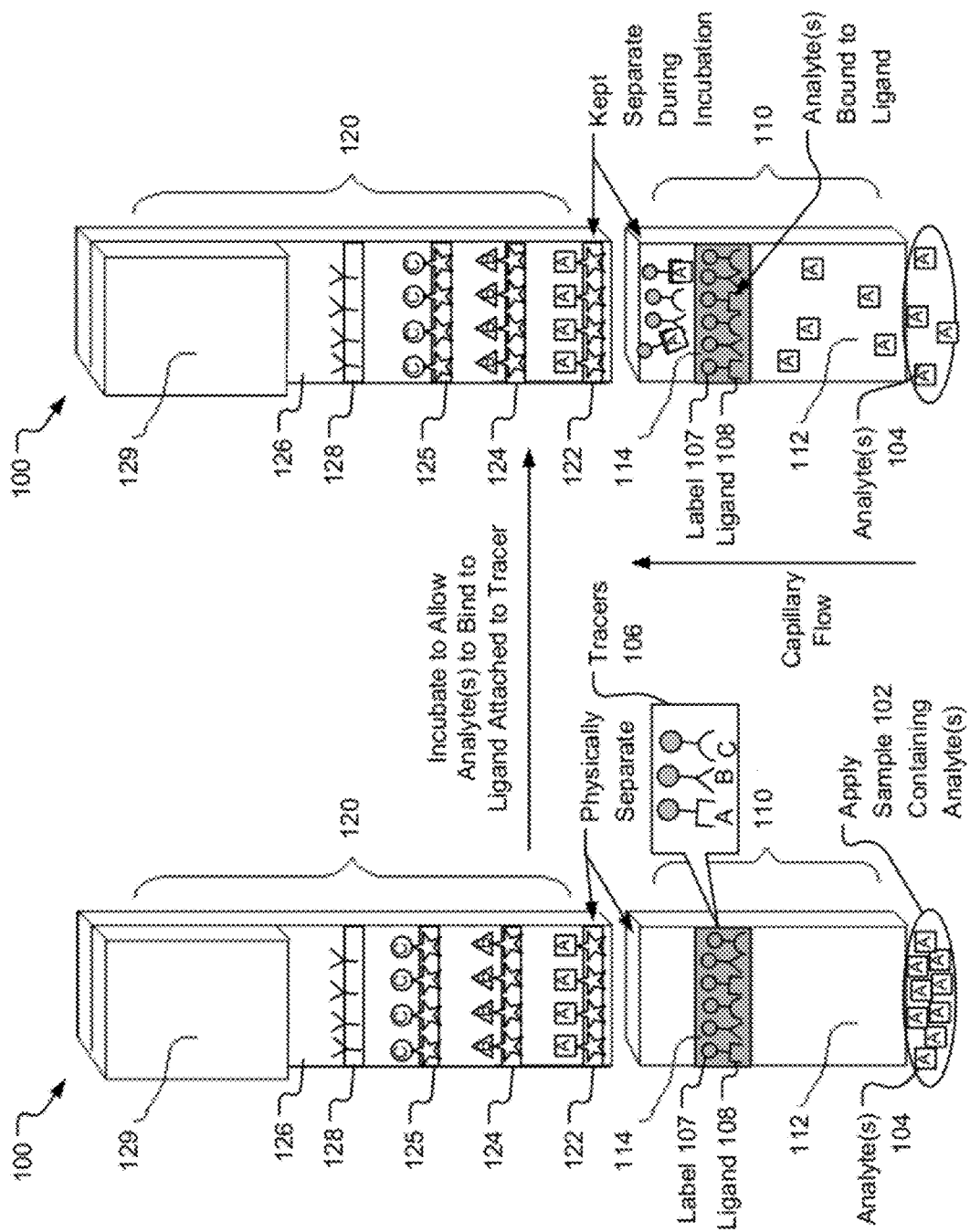
FIG. 1A is a block diagram showing an example of a using a discontinuous capillary flow assay device to detect type A analytes.

Techniques, materials, apparatus and systems are described for implementing a lateral capillary flow assay to identify a presence of analytes in a sample. A capillary flow assay device can be implemented to temporarily discontinue the capillary flow to control the incubation time between the analytes and the binding ligands present in the assay device. By controlling the incubation time, the analytes are given the proper opportunity to bind to the binding ligands, which can improve the assay test sensitivity. For example, the discontinuous capillary flow assay device can include two separate pieces of absorbent materials. The capillary flow across the two pieces can be interrupted by keeping the two pieces physically separated to enhance the incubation period. Then, the two pieces can be brought together to allow the capillary flow to continue across the two pieces. Additionally, a physical barrier can be positioned between the two function areas of a single united test strip to slow down the capillary flow across the two pieces. The barrier material can include a dissolvable or permeable agent that inhibits or delays the capillary flow, which is re-established after a set time period or delay.

FIGS. 1A, 1B, 1C, 1D and 1G are block diagrams of different examples of a discontinuous (e.g., multiple component) capillary flow assay device. The capillary flow assay device for detecting analytes in a sample can include multiple solid support portions having at least four distinct areas. The first area is designed for receiving a sample that may or may not include analytes. The second area contains tracers or indicators that selectively bind to the analytes. The sample solution flows to the tracer holding area by capillary force, causing the tracer to co-flow with the sample on the support portions and allows any analytes present in the sample to bind to the ligands on the tracer material. The third area contains at least one type of binder material that is immobilized to the solid support portion. The binder material can specifically bind to the tracer material or the analytes or both directly or indirectly. The fourth area includes a validation area that includes binder materials that bind to the indicator material of label-ligand conjugate (e.g., antibody against antibody, such as goat-anti-mouse) to confirm that the indicator material properly flowed across the capillary flow assay device. The fifth area, located at the flow end of the second solid support portion, can include an absorbent material that receives and stores liquid containing any analytes and tracer materials that flow through the solid support portions. After sample loading, the sample mixes with the tracer material during a controlled incubation period; the different portions of the device are brought in physical contact with each other; and the tracer material is detected (or not detected) at the binder holding areas (binding sites) in a dynamic flow to determine whether the sample contains any analytes. The entire assay can complete in 5 to 15 minutes.

For example, FIG. 1A shows an example of a discontinuous capillary flow assay device 100. The discontinuous capillary flow assay device 100 includes multiple capillary flow support portions 110 and 120. The capillary support portions 110 and 120 can be made of a porous or absorbent material that allows capillary flow of a liquid sample along with any analytes in the liquid sample. The absorbent material used in the device can include any one or combination of materials that can transport a liquid sample by capillary action, such as nitrocellulose, glass fiber, cellulose, nylon, etc.

A first capillary flow support portion 110 includes a sample receiving area 112 to receive a sample to be analyzed, and a tracer or indicator material holding area 114 to house one or more types of indicator materials 106. Different types of the tracer or indicator material 106 can be included based on the types of target analytes that may be present in the sample. For illustrative purposes, three different types (A, B, C) of indicator material are shown in FIG. 1A. However, the number of different types of indicators materials included can vary (e.g., less than 3 or more than 3) based on the number of analytes to be tested. The indicator type A includes a label 107 and a ligand 108 that binds to type A analyte. The indicator type B includes a label 107 and a ligand 108 that binds to type B analyte. The indicator type C includes a label 107 and a ligand 108 that binds to type C analyte. The types A, B and C can represent different types of small particles, such as different types of drug compounds, for example. The label 107 and the ligand 108 can be formed as a label-ligand conjugate. The first capillary flow support portion 110 can be implemented as a single piece or multiple pieces, one for each area (e.g., a sample receiving area and an indicator receiving area) that can be connected together prior to performing an assay. Also, the first capillary flow support portion 110 can be implemented as a single piece that includes the sample receiving area 112 and the indicator holding area 114.

A second capillary action support portion 120 can be made of an absorbent or porous material 126. The absorbent or porous material used for the second capillary action support portion 120 can be the same or different material as the first capillary action support portion 110. The second capillary action support portion 120 includes multiple binder material holding areas 122, 124 and 125 that each hold different types of binder materials. For example, the binder material holding area 122 can house at least one type of binder material (e.g., type A) immobilized to the second capillary action support portion 120. The binder material holding area 124 can house another type (e.g., type B) of binder material immobilized to the second capillary action support portion 120. The binder material holding area 125 can house yet another type (e.g., type C) of binder material immobilized to the second capillary action support portion 120. The number of different binder material holding area can correspond to the number of indicator types present in the first capillary action support portion 110. The different types of binder material can selectively bind to the corresponding tracer or indictor material or the analyte. For example, the type A binder material can bind to the indicator material with type A binding ligand. Additionally, the second capillary action support portion 120 can include additional binding material holding areas to hold additional types of binding material. For example, the number of different binder material holding areas can range from 1 to 8.

Additionally, the second capillary action support portion 120 can include a capture or validation area 128 that includes a ligand or a binder material that selectively binds to the indicator material of label-ligand conjugate (e.g., antibody against antibody, such as goat-anti-mouse) to confirm that the indicator material properly flowed across the capillary flow assay device. The second capillary action support portion 120 can also include an area of absorbent material to receive and store any analyte, tracer material or both that flow across both portions 110 and 120.

The tracer or indicator material 106 can include a ligand 108 attached to a label 107 that can be measured. The label 107 and the ligand 108 can form a label-ligand conjugate. The ligand 108 can include a chemical substance that selectively binds, or is bound by an analyte, a binder material or both. Similarly, an analyte can include a chemical substance that selectively binds, or is bound by, the ligand, a binder material or both. The label 107 can include a measurable or identifiable agent, such as a gold colloidal material, a latex nanoparticle, an iron nanoparticle or enzyme, a fluorescent material, a chemiluminescent material, or similar chemical labels that is directly or indirectly linked to the ligand. Based on a particular assay design, each analyte, the ligand on the tracer or the binder material can have distinct characteristics and binding specificities.

For example, the analyte can be a small or large molecule that acts as a target for an antibody or another molecule to specifically bind to the analyte. For such example, the ligand on the tracer material can act as the antibody or another molecule and the binder material immobilized to the second capillary action support portion 120 can act similarly as the analyte to competitively bind to the ligand. The binder material can be directly immobilized to the support portion 120 or indirectly immobilized by conjugating to a large carrier molecule.

As shown in FIG. 1A, a user can apply a sample liquid 102 to the first portion 110 and incubate the first portion in the sample liquid. On the left-hand side of FIG. 1A, the sample liquid 102 containing analytes of type A is applied to the sample receiving area 112 of the first portion 110. The first portion 110 and the second portion 120 are physically separated to allow the tracer material 106 to incubate with the analytes in the sample. On the right-hand side of FIG. 1A, the device has been incubated in the sample liquid and the analytes have flowed toward the tracer material 106 holding area 114 by capillary action. Due to the incubation time, the type A analytes can selectively bind to the type A tracer material 106 with the ligand 108 that selectively binds to the type A analyte. Because the binding time of analytes to the tracer material 106 can vary based on the analyte types, a user can vary the incubation time by keeping the first portion 110 and the second portion 120 physically separated for a desired period of time. The type A tracer material 106 bound to the type A analytes in the sample continues to flow across the first portion 110 but is prevented from flowing across to the second portion 120 by a physical barrier (e.g., physically separated). The other types of indicator materials 106 (e.g., type B and type C) remain unbound because the sample liquid does not contain type B or type C analytes.

In competitive binding, where the analyte and the binder material compete to bind with the ligands on the tracer material, the binding time for the analyte to interact with the ligands can be longer than the travel time for the ligands to flow to the binder material holding areas (e.g., the binding site). If the concentration of the analyte(s) in the sample is low enough or the binding affinity is low or both, a capillary flow assay device may not adequately detect the presence or absence of the analyte. For example, the content of the hydrophobic delta-9-tetrahydrocannabinol (Δ9-THC), the parent form of illicit drug marijuana in saliva, decreases rapidly in the first a few hours after marijuana smoking. The concentration of Δ9-THC can drop from hundreds or thousands nanogram (ng) per milliliter (ml) down to less than ten ng per ml. It can be difficult to detect Δ9-THC in saliva at this concentration, making it impractical to perform a capillary flow assay for detecting the mostly consumed illicit drug without an adequately long incubation period that allows the analyte to bind to the tracer material. Thus, a continuous flow with very short incubation time between the THC analyte and the tracer (e.g., anti-THC antibody-label) greatly can limit the test sensitivity. Additionally, the hydrophobic nature of the sample can cause the analyte(s) to be lost (e.g., stickiness of the sample can cause the analytes to get stuck to a surface of the device). Moreover, the relatively low binding affinity of anti-THC antibodies can reduce the sensitivity of an assay for determining analytes at low concentrations. For at least these reasons, the device 100 includes multiple portions (e.g., 110 and 120) that are physically separated (e.g., discontinuous) to allow for adequate incubation periods.

Depending on the nature of the analyte, reaction conditions and the antibody affinity, an ideal incubation time can be controlled to obtain maximum binding between the analyte and the tracer. For many, short incubation time can be enough to meet the sensitivity need of the assay. For others, a few minutes of prolonged incubation time can greatly improve the sensitivity.

The incubation time can be as short as a minute or two, and the incubation process can be integrated with the sample collection process so as to not extend the total assay time. In some implementations, the incubation time between the analyte and the tracer can be prolonged up to 10 hours, before the two portions 110 and 120 are engaged.

Figure 1B:
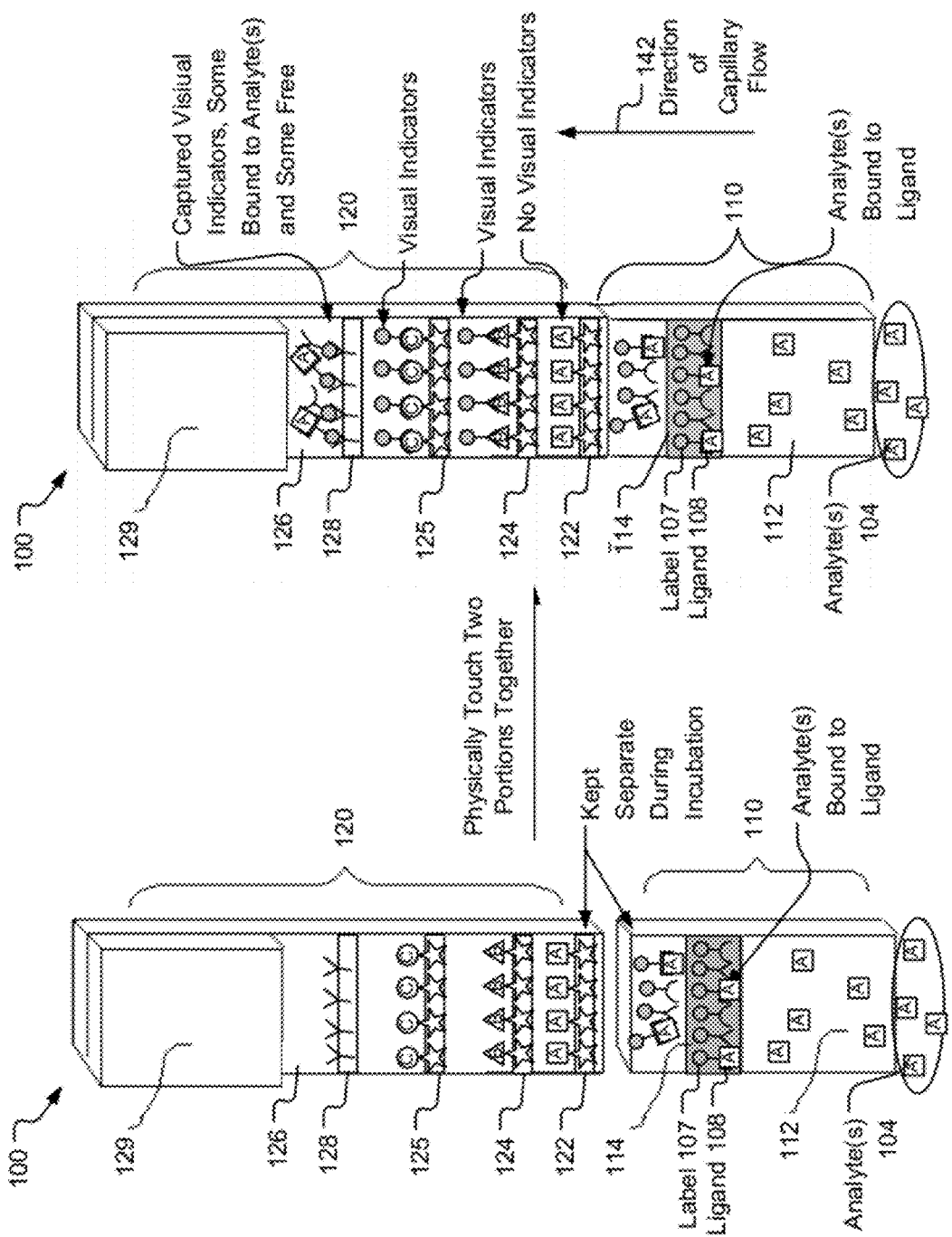
FIG. 1B is a block diagram that shows a process of combining two separate portions of a test strip after an incubation period to detect type A analytes.

FIG. 1B shows combining the two portions 110 and 120 after an incubation period. The left-hand side shows the device 100 incubated in the sample liquid as described above. After an incubation period controlled by the user, the two portions 110 and 120 are brought in physical contact with each other. The type A tracer material 106 with the type A ligands 108 bound to the type A analytes flow from the first portion 110 across to the second portion 120. When the type A tracer material 106 with the type A analytes from the sample bound to the type A ligands 108 reach the binder material holding areas 122, 124 and 125, the type A ligands 108 can not bind to the immobilized type A binder material in area 122 because the binding sites on the ligands 108 are already occupied by the analytes from the sample. Therefore, the tracer material 106 with the analytes bound to the ligands 108 does not stop at the binder material holding areas 122 and 124. This is an example of competitive binding of the analytes and the binder material with the tracer material 106. Because the type A indicator material did not stop at area 122, no visual indication is visual to the naked eye.

However, the type B and type C indicator materials have unbound ligands and thus can bind to the type B binder material in area 124 and type C binder material in area 125. Because the types B and C indicator materials are immobilized to areas 124 and 125, visual indications (e.g., brownish color of gold colloid are visible at areas 124 and 125.

The type A tracer material 106 bound with the type A analytes continues to flow laterally by capillary action until captured at the capture or validation area 128. The unbound tracer material 106 (e.g., types B and C) also flow laterally by capillary action until captured at the capture or validation area 128. The label 107 attached to the ligand 108 of the tracer material 106 allows the detection of the tracer material 106 at the capture or validation area 128 by visual inspection or other means. For example, the gold colloidal material has a reddish color that can be visually detected by the naked eye. Detection of the tracer material 106 at the capture or validation area 128 allows the user to confirm that the device performed properly and the capillary action carried the tracer material 106 from the first portion 110 to the second portion 120. The absence of the tracer material 106 (e.g., no red color) at the binder material holding area 122 indicates that the sample liquid contained the type A analytes. The presence of indicator material 106 at areas 124 and 125 indicates that the sample liquid did not include type B and type C analytes. Moreover, the absorbent material at area 129 collects and contains the remaining liquid that flowed across the two portions of the capillary flow assay device 100.

Figure 1C:
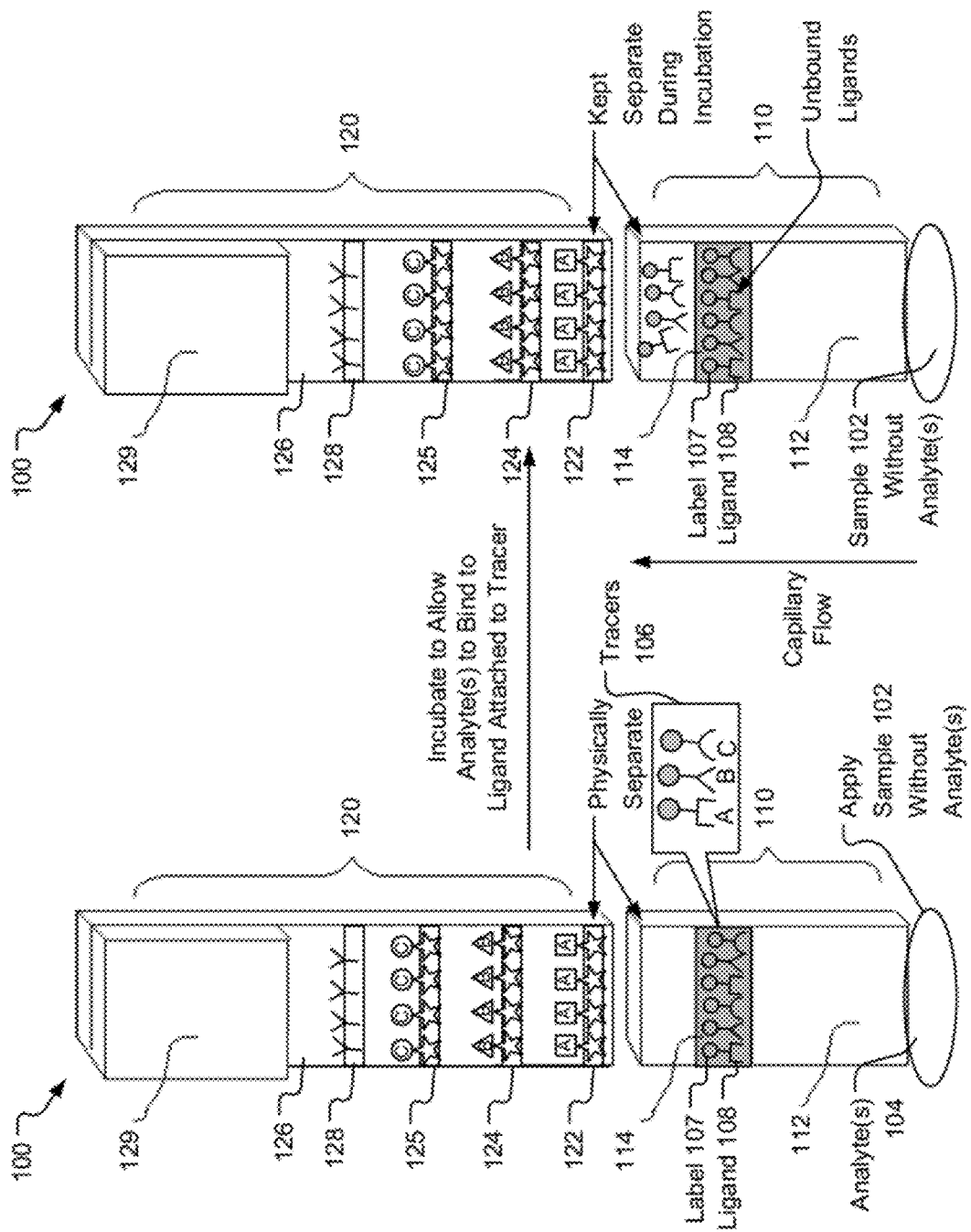
FIG. 1C is a block diagram that shows a process of applying a sample liquid that does not contain any analytes to a discontinuous capillary flow assay device.

FIG. 1C shows applying a sample liquid that does not contain any analytes to the device 100. The left-hand side shows the device 100 with the sample (sans analytes) applied to the sample receiving area 112. The two portions 110 and 120 are physically separated while the device is incubated in the sample. The right-hand side shows the device 100 with the tracer material 106 with the analyte-free ligands moving across the first portion 110 by capillary action. Because the two portions 110 and 120 are physically separated, the tracer material cannot flow across to the second portion 120.

Figure 1D:
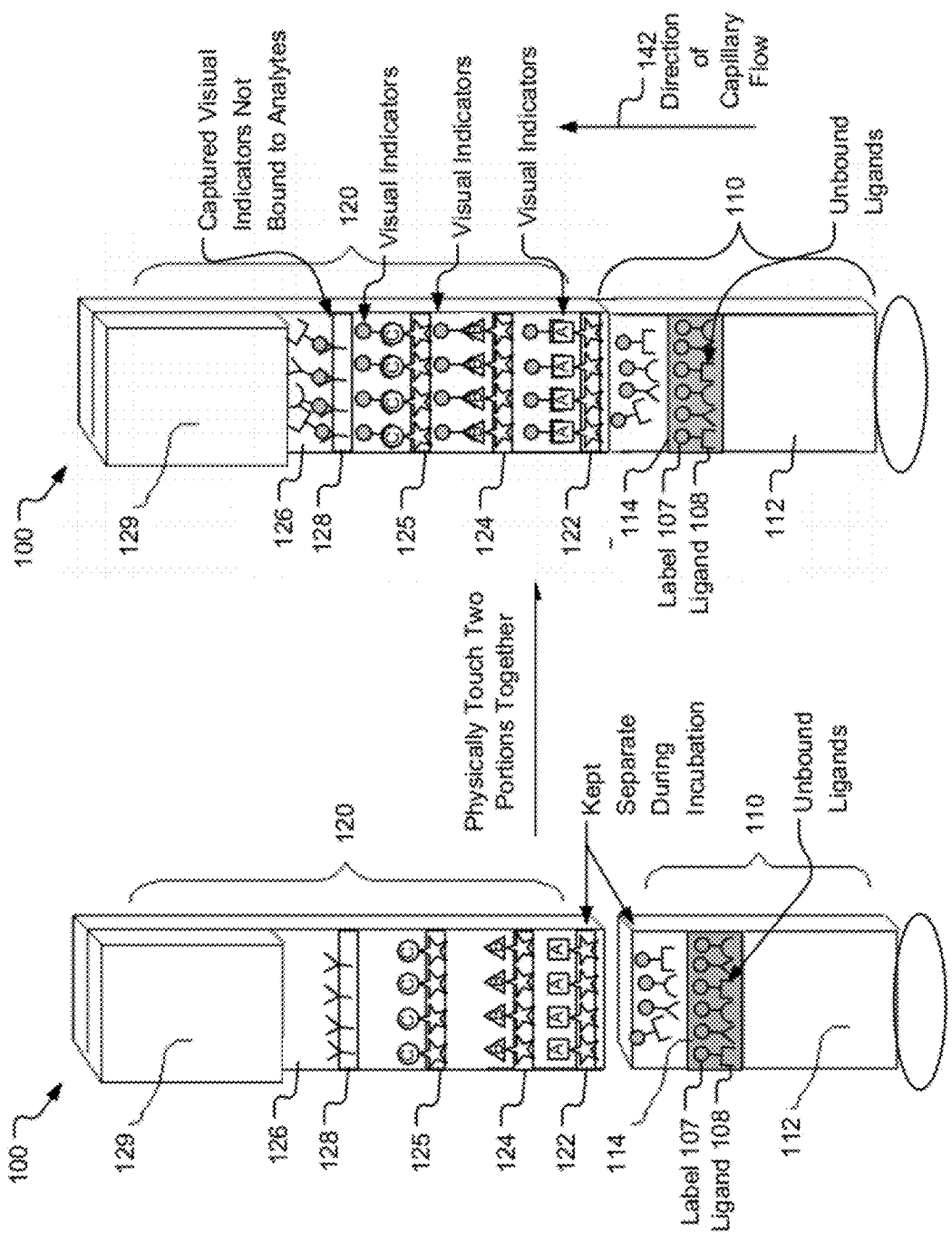
FIG. 1D is a block diagram that shows a process of bringing together two portions of a test strip in physical contact with each other in absence of any analytes.

FIG. 1D shows bringing together the two portions 110 and 120 in physical contact with each other. The unbound (e.g., analyte-free) tracer material 106 (e.g., all three types A, B and C) move across to the second portion 120 and continue to move through the second portion 120 by capillary action. The binder materials immobilized to the second portion 120 at the binder holding areas 122, 124 and 125 competitively bind to the unbound ligands 108 of the tracer material. Because the binder materials are immobilized, the tracer material 106 bound to the binder materials stops at the binder holding areas 122, 124 and 125. The labels attached to the types A, B and C ligands of the tracer materials can be detected as described above. For example, a presence of a red color at the binder holding areas 122, 124 and 125 indicates that the sample liquid is free of the types A, B and C analytes.

Any unbound tracer materials continue to flow laterally through the second portion 120 until captured at the capture or validation area 128. As described above, the detection of the tracer material 106 (e.g., red color at area 128) indicates that the device operated properly and the tracer material 106 flowed from the first portion 110 to the second portion 120 by capillary action.

FIG. 1E shows an example of detecting type B analytes in a sample liquid. In this example, the indicator material is visible only at areas 122 and 125. The lack of indicator material at area 124 indicates that the sample liquid included the type B analytes. The presence of indicator materials at areas 122 and 125 indicates that the sample liquid did not include types A or C analytes. The presence of indicator material at the validation area 128 confirms that the device functioned properly.

FIG. 1F shows an example of detecting type C analytes in a sample liquid. In this example, the indicator material is visible only at areas 122 and 124. The lack of indicator material at area 125 indicates that the sample liquid included the type C analytes. The presence of indicator materials at areas 122 and 124 indicates that the sample liquid did not include types A or B analytes. The presence of indicator material at the validation area 128 confirms that the device functioned properly.

FIG. 1G shows an example of detecting a combination of different analyte types (e.g., type B and type C) in a sample liquid). In this example, the indicator material is visible only at area 122. The lack of indicator material at areas 124 and 125 indicates that the sample liquid included the types B and C analytes. The presence of indicator materials at area 122 indicates that the sample liquid did not include type analytes. The presence of indicator material at the validation area 128 confirms that the device functioned properly.

FIG. 1H shows an example of detecting all of the different types present in a sample liquid. In this example, the indicator material is not visible at any of the areas 122, 124 or 125. The lack of indicator material at areas 122, 124 and 125 indicates that the sample liquid included the types A, B and C analytes. The presence of indicator material at the validation area 128 confirms that the device functioned properly.

The device 100 can implement different binding interactions other than the competitive binding described above. For example, the target analyte can include a large molecule that contains same or different structures at different locations on the large molecules. For such an analyte, the ligands on the tracer material can be selected to include an antibody or other chemical material that can specifically bind to one of the structures on the large molecule. Then the binder material can be selected to include another antibody or other chemical material that can specifically bind to another structure on the large molecule. This type of a binder material can capture the analyte bound to the tracer material that moves by capillary flow. The resulting complex is a "sandwich" complex at the binder holding area (e.g., the binding site), and the bound sandwich complex is detectable at the binding site.

FIG. 1I shows another example of a discontinuous capillary flow device. The device 180 includes the different areas including a sample receiving area 112, a tracer holding area 114, one or more binder material holding areas 122, 124 and 125 and a capture or validation area 128. Additionally, the device 180 can be implemented as multiple portions with a barrier portion 182 that connects the first portion with the second portion. The barrier portion 182 can include materials (e.g., soluble material) that slows down capillary flow between the first and second portions until the barrier portion 182 is removed, for example.

FIG. 1J shows an example of an integrated capillary flow device comprising a single unit. The integrated capillary flow device 190 includes all of the same areas as those described with respect to FIGS. 1A-1I. However, two portions of the capillary flow device described in FIGS. 1A-1I are configured as a single unified unit.

As shown in FIGS. 1A-1J, the discontinuous and integrated capillary flow assay devices (e.g., 100, 180 and 190) can detect the presence or absence of an analyte. Also, the device can detect the amount of the analyte(s) in a sample by detecting the presence or absence of the tracer or indicator bound to the binder directly or indirectly.

FIGS. 2A, 2B and 2C are diagrams of various sample collectors. For example, FIG. 2A shows a sample collector 200 that includes a handle 202 and a collection mechanism 204. The collection mechanism can include an absorbent material that absorbs a sample on contact. For example, a user can hold the sample collector 200 by the handle 202 and touch the collection mechanism 204 against a sample liquid, such as the saliva, urine, blood, etc. of a test subject. After the sample is collected, collector 200 can be inserted into a sample retaining device to retain the sample for confirmation testing, for example. A sample retaining device is described further with respect to FIGS. 3A and 3B below.

FIG. 2B shows a sample collector 210 that contains an assay device (e.g., test strip). The sample collector 210 includes a handle 202 and a collection mechanism 204 as described with respect to FIG. 2A. In addition, the sample collector 210 includes an assay device (e.g., test strip) 206 inside the sample collector 210. For example, the assay device (e.g., test strip) 206 can be placed inside the handle 202. The assay device (e.g., test strip) 206 can be implemented as a single continuous device or separate discontinuous or disconnected devices. The assay device (e.g., test strip) 206 can be implemented in a similar fashion as the first capillary flow support portion 110 and the second capillary flow support portion 120 combined. Additionally, the sample collector 210 can include a window or a display portion 208 on the handle 202 for presenting information associated with the assay test result.

FIG. 2C shows a sample collector 220 that contains an assay device (e.g., test strip) implemented as two separate pieces 222 and 224. The sample collector 210 includes a handle 202 and a collection mechanism 204 as described with respect to FIGS. 2A and 2B. In FIG. 2C, the sample collector 220 includes an assay device (e.g., test strip) in two pieces 222 and 224 placed inside the sample collector 220. For example, a first piece 222 can be placed inside the collection mechanism 204, and a first piece 224 of the assay device (e.g., test strip) can be placed inside the handle 202. The second piece 224 can be implemented in a similar fashion as the second capillary action support portion 120 in FIG. 1A. The first piece 222 of the assay device (e.g., test strip) can be implemented in a similar fashion as the first capillary flow support portion 110 in FIG. 1A that includes a sample receiving area 112 to receive a sample to be analyzed, and a tracer or indicator material holding area 114 to house one or more indicator materials. When the collection mechanism 204 collects a sample particle, the first piece 222 can be used to incubate the sample particles with the tracer to allow for binding. Because the first piece 222 is physically separated from the second piece 224, capillary action initially stops at the boundary of the first piece 222. A user can bring together the two pieces 222 and 224 to resume capillary action across the two pieces and perform a desired assay as described with respect to FIGS. 2D-2E below. Additionally, the sample collector 220 can include a window or a display portion 226 on the handle 202 for presenting information associated with the assay test result.

FIG. 2D shows a sample retaining devices 230 that can interact with a sample collection device to receive and retain a sample. The sample collection device 220 includes handle 202 and a collection mechanism 204 as described above. A user can hold the sample collection device 220 by the handle 202 and insert the collection mechanism 204 into an (or sample chimney) 232 of a retaining device 230. The retaining device 230 can include a filtering unit 234, such as a sieve, a screen, a mesh, etc. to filter a liquid received through the (or sample chimney) 232. When a user pushes the collection mechanism 204 of the sample collection device 220 against the filtering unit 232 of the retaining device 230, the two pieces 222 and 224 of the assay device (e.g., test strip) are pushed together and come in physical contact with each other. For example, the absorbent material of the collection mechanism can become depressed and the first piece 222 of the assay device (e.g., test strip) can be pushed toward the second piece 224.

In addition, the filtering unit 232 can filter out large particles that are visible to the naked eye and allow smaller particles along with any liquid into a sample retaining area 236 of the retaining device 230. The sample liquid in the sample retaining area 236 of the retaining device 230 can be stored by placing a cap over the (or sample chimney) 232 of the retaining device. The stored sample liquid can be tested for the presence of a given target analyte. Such testing can be used to confirm the results obtained from the assay device (e.g., test strip) pieces 222 and 224.

FIG. 2E shows another sample retaining devices 240 that can interact with a sample collection device to receive and retain a sample. The sample retaining device 240 can be implemented in a similar manner as the sample retaining device 230 but with a different overall shape. For example, the sample retaining device 240 can include a filtering unit 244, such as a sieve, a screen, a mesh, etc. to filter a liquid received through the (or sample chimney) 242. The sample retaining device 240 can interface with the sample collection device 220 in a manner similar to the one illustrated in FIG. 2D.

Figure 3A:
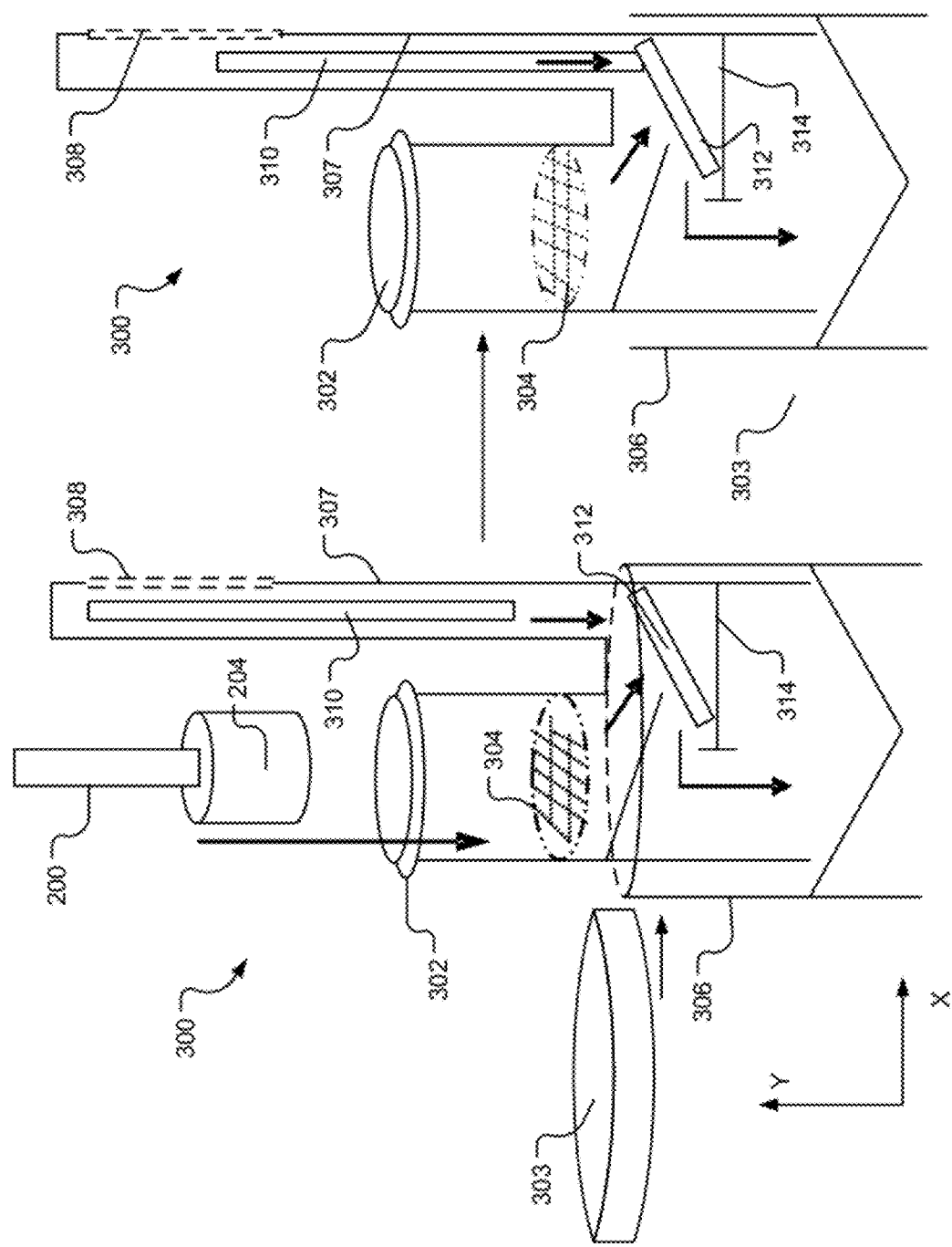
FIG. 3A shows a design or implementation of a capillary flow assay device or system that combines sample collection and testing.

FIG. 3A shows a design or implementation of a capillary flow assay device or system 300 that combines sample collection and testing. The capillary flow assay device or system 300 can include a sample collector receiving unit (or sample chimney) 302, a filtering unit 304, a sample retaining or housing unit 306, a testing unit housing and display unit 307, a testing unit inlet 308, two separate pieces 310 and 312 of testing unit (e.g., two test strips) and a sample reservoir or well 314. A user can obtain a sample liquid using a sample collection unit 200. The sample collection unit 200 may not include an testing unit (e.g., test strip) as illustrated in FIG. 2A. The user can insert the sample collection unit 200, with the obtain sample liquid absorbed in the collection mechanism 204 of the sample collection unit 200, into the sample collector receiving unit (or sample chimney) 302. The sample receiving unit 302 is shaped to easily engage or interface with the sample collection unit 200. As the user pushes the collection mechanism 204 of the sample collection unit 200 against the filtering unit 304, the sample liquid can flow from the absorbent material of the collection mechanism 204 and through the filtering unit 304 to the sample reservoir or well 314. Once the sample reservoir or well 314 is filled, the sample liquid can overflow into the sample retaining unit 306.

The first piece 312 of the testing unit (e.g., a first test strip) can be implemented in a similar fashion as the first capillary flow support portion 110 in FIG. 1A that includes a sample receiving area 112 to receive a sample to be analyzed, and a tracer or indicator material holding area 114 to house one or more indicator materials. The first piece 312 of the testing unit (e.g., a first test strip) can be in contact with and receive the sample liquid in the well 314 into a sample receiving area (similar to sample receiving area 112 in FIG. 1A). The first piece 312 can be placed in the well 314 in such a way that only one end of the first piece 312 is in the well and in contact with the sample liquid in the well 314. For example, the sample receiving area 112 of the first piece 312 can be in contact with the sample liquid in the well. A given analyte present in the sample liquid moves by capillary action towards a tracer material holding portion (similar to tracer material holding portion 114 in FIG. 1A) as described with respect to FIGS. 1A-1G. A given analyte present in the sample can bind and co-flow with the tracer material to the end of the first piece 312.

For the two strips discontinuous design or implementation shown in FIG. 3A, after a desired incubation time to allow a given analyte present in the sample to bind with the tracer material in the first piece 312, the user can engage the second piece 310 of the testing unit (e.g., a second test strip) to be in physical contact with the first piece 312 of the assay device (e.g., a first test strip) to allow a given analyte that bound with the tracer material to flow towards binder material on the second piece 310. The capillary movement of analytes across the two pieces 312 and 310 of the testing unit (e.g., two separate test strips) can be implemented in a manner similar to the first and second capillary flow support portions 110 and 120 as shown in FIGS. 1A-1H. The result of the assay can be visualized using the testing unit housing and displaying unit 307. The testing unit housing and displaying unit 307 can be made of a material that allows at least visual light to pass through and make the second piece 310 of the testing unit visible to a user. When the indicator materials are visible at different areas of the second piece 310, the colored label of the indicator material can be seen through the testing unit housing and displaying unit 307. The materials for the testing unit housing and displaying unit 307 can include glass, plastic, polymer materials, or any other materials that allow at least visual light to pass through.

Moreover, the capillary flow assay device 320 can include a testing unit inlet 308 to receive a replaceable second piece 310 of the testing unit. Through the testing unit inlet 308, a user can insert different types of the second piece 310, each one having different types of binding materials. Because a single second piece 310 of the testing unit may not be able to include all of the desired number of binding materials need to test for all of the desired number of analytes, a user can insert one at a time until all of the desired numbers of analytes have been tested. The testing unit inlet 308 can be placed on a surface of the testing unit housing and displaying unit 307 that is parallel to the Y-axis.

The right-hand side of FIG. 3A shows adding a cap 303 to seal the sample inlet 302 and moving the second piece 310 of the testing unit to be in physical contact with the first piece 312 of the testing unit. For example, after a desired period of incubation, the user can insert a desired second piece 310 (with the desired types of binder material) into the testing unit inlet 308 and move the second piece 310 to be in physical contact with the first piece 312. Once, the two pieces 312 and 310 come in contact with each other, a given analyte absorbed into the first piece 312 moves across the second piece 310 by capillary flow.

FIG. 3B shows an example of storing the sample liquid in a sample retaining unit. As described above, once the sample reservoir or well 314 is filled, the sample liquid can overflow into the sample retaining unit 306. The sample retaining unit can be physically separated from rest of the capillary flow assay device. A cap 303 can be used to seal the sample retaining unit and store the sample liquid for later use (e.g., such as performing addition testing with the retained sample liquid to confirm the results of the test strips. The sample retaining unit 306 and the cap 303 as illustrated and described in FIG. 3B can be substantially the same for the other capillary flow assay devices of FIGS. 3C-3L.

Figure 3D:
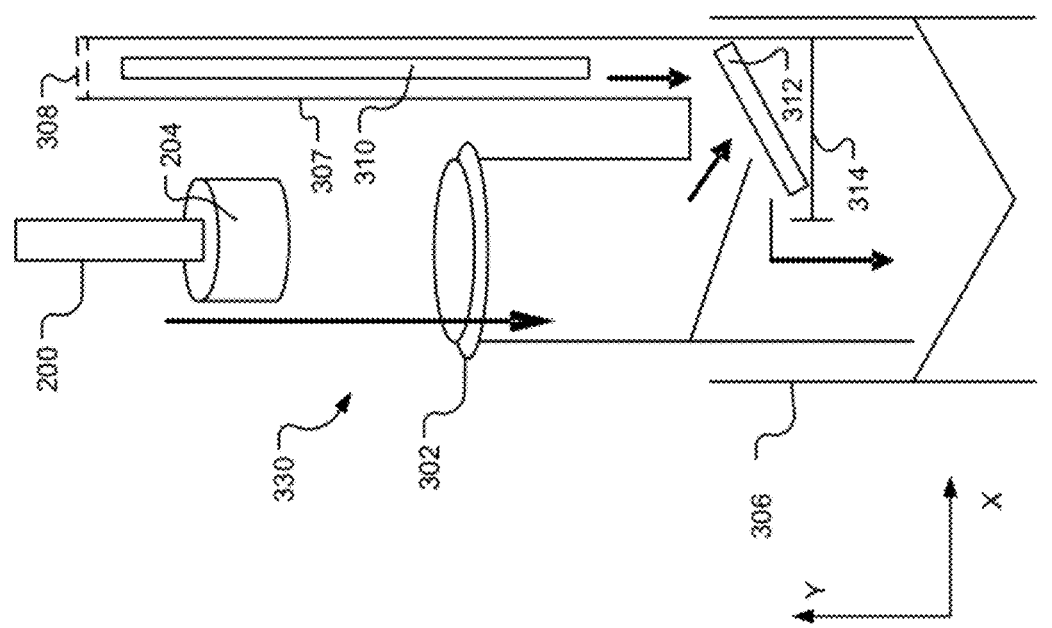
FIG. 3D shows yet another example of a capillary flow assay device or system without a filtering unit a testing unit inlet placed at a top surface of a testing unit housing unit.
Figure 3C:
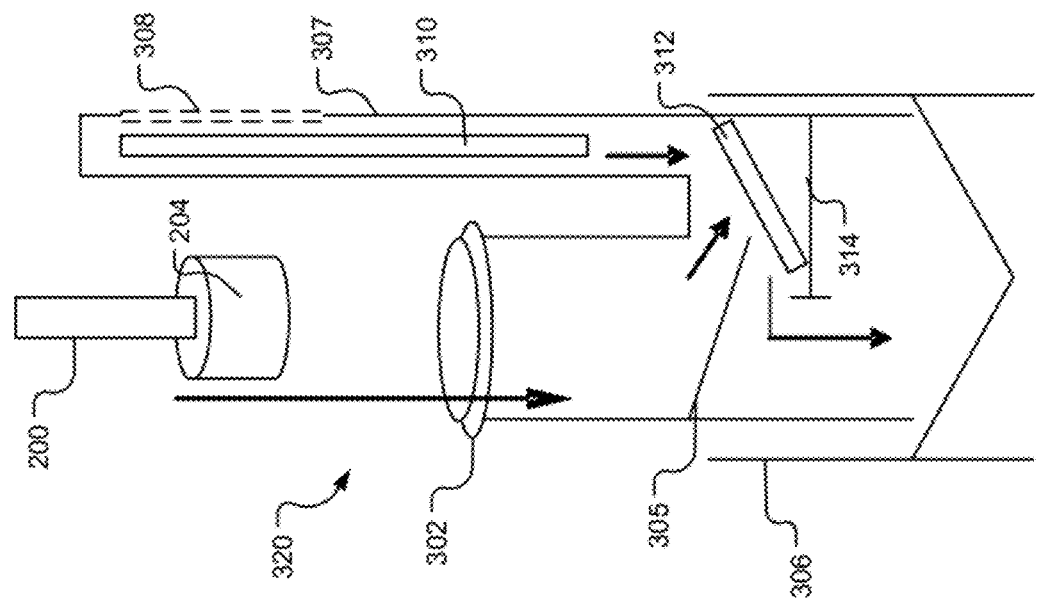
FIG. 3C shows another example of a capillary flow assay device or system without a filtering unit.

FIG. 3C shows another example of a capillary flow assay device or system. The device or system 320 shown in FIG. 3C is similar to the one shown in FIGS. 3A and 3B. However, the filtering unit 304 has been made optional and thus removed from the figure. When the filtering unit 304 is absent from the device or system, the sample collecting unit 200 can be pressed against a bottom 305 of the sample inlet 302 to squeeze the sample liquid from the absorbent material 204 of the sample collecting unit 200. In all implementations and Figures, the bottom 305 of the sample inlet 302 can be angled to allow the sample liquid to flow down to the well 314.

FIG. 3D shows yet another example of a capillary flow assay device or system. The device or system 330 shown in FIG. 3D is similar to those in FIGS. 3A-3C. However, the filtering unit is made optional and the testing unit inlet 308 is placed at a top surface of the testing unit housing unit 307. The top surface of the testing unit housing unit 307 is a surface that is parallel to the X-axis.

Figure 3E:
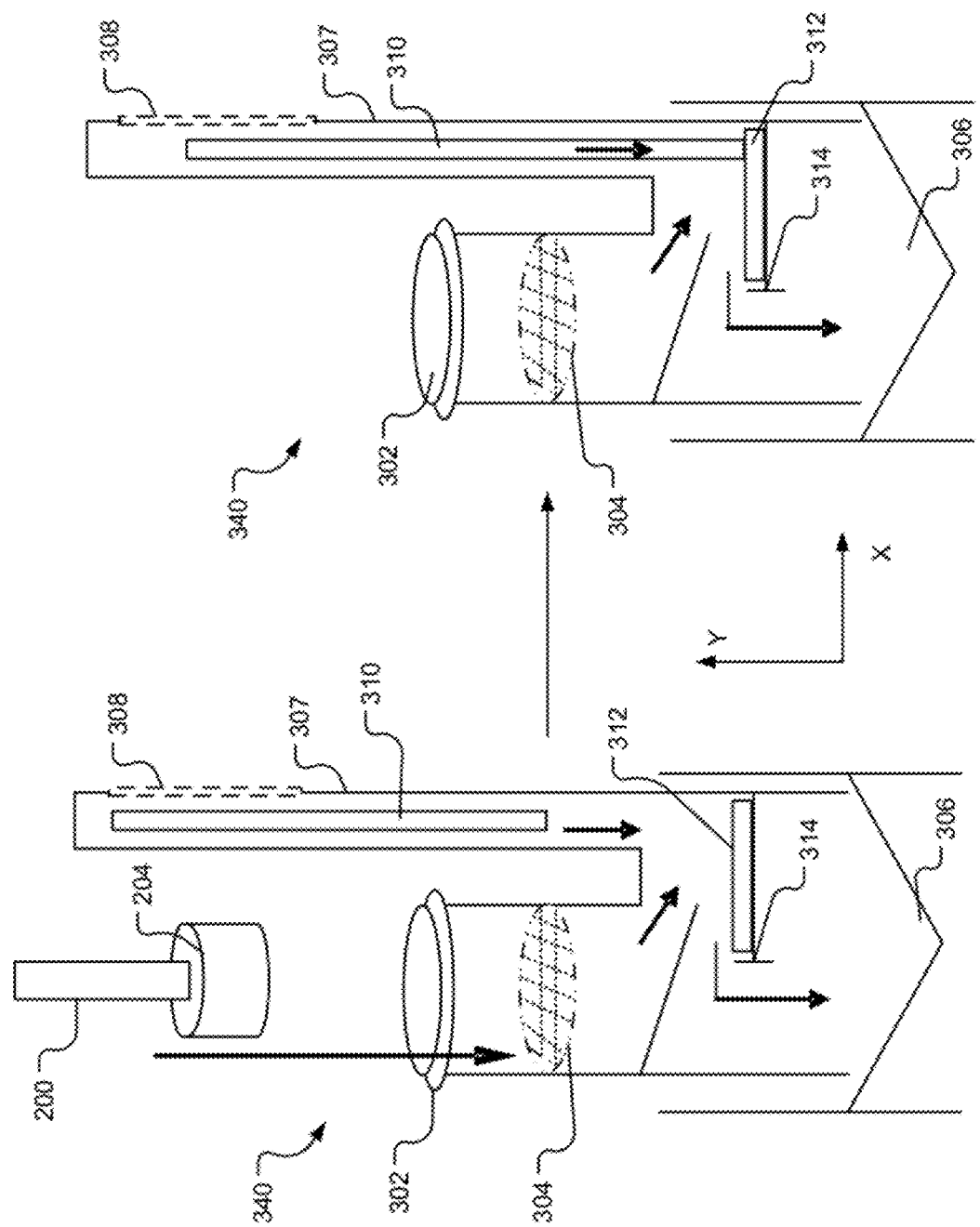
FIG. 3E shows yet another design or implementation of a capillary flow assay device or system with a first piece of a testing unit placed in a well in such a way that an entire first piece can come in contact with a sample liquid in the well.

FIG. 3E shows yet another design or implementation of a capillary flow assay device or system 340. The device or system 340 in FIG. 3E is similar to the those shown in FIGS. 3A-3D, including the optional filtering unit 304. However, the first piece 312 of the testing unit is placed in the well 314 in such a way that the entire first piece can come in contact with the sample liquid in the well 314. FIG. 3F shows yet another design or implementation of a capillary flow assay device or system 350 that is similarly structured as the one shown in FIG. 3E. However, the filtering unit 304 is optional and thus removed form the figure. FIG. 3G shows yet another example of a capillary flow assay device or system. The device or system 360 shown in FIG. 3G is similar to those in FIGS. 3B, 3E and 3F. However, the filtering unit is made optional and the testing unit inlet 308 is placed at a top surface of the testing unit housing unit 307. The top surface of the testing unit housing unit 307 is a surface that is parallel to the X-axis.

In some implementations, the testing unit can be implemented as a single integrate unit. For example, FIG. 3H shows an example of a capillary flow assay device or system 370 that uses a testing unit that integrates the first piece 312 and the second piece 310 of FIGS. 3A-3G as a single unit. The single unit testing unit in FIG. 3H can be implemented similar to the test strip in FIG. 1I that includes a barrier layer to allow an incubation period. Also, the single unit testing unit in FIG. 3H can be implemented similar to the test strip in FIG. 1J that does not include a barrier layer. FIG. 3I shows another design or implementation of a capillary flow assay device or system 380 that uses a single unit testing unit. The design or implementation in FIG. 3I is similar to the one in FIG. 3H. However, the optional filtering unit 304 is included. The testing unit housing and displaying unit 307 in FIGS. 3H and 3I can be implemented similar to those in FIGS. 3A-G to allow the user to see the second piece 310 through the housing unit. The testing unit inlet 308 in FIGS. 3H and 3I can be placed on a surface of the testing unit housing and displaying unit 307 similar to those in FIGS. 3A-F.

FIG. 3J shows yet another design or implementation of a capillary flow assay device 390 that uses a single unit testing unit. The device or system 390 in FIG. 3J can be implemented similar to those in FIGS. 3H and 3I. However, the device or system 390 does not include the optional filtering unit 304. Additionally, the device or system 390 includes the testing unit inlet 308 placed on a top surface similar to those shown in FIGS. 3D and 3G.

FIG. 3K shows yet another design or implementation or implementation of a capillary flow assay device or system that uses a single unit testing unit. The device or system 390 is implemented similar to those in FIGS. 3H-J. However, the device or system 390 does not include a testing unit inlet because the single unit testing unit can be built into the device or system and is not replaceable or removable. In some implementations, the device or system in FIGS. 3A-3G can also be implemented to have the first piece 312 and the second piece 310 built into the device of system, and thus can exclude the testing unit inlet 308.

In some implementations, a capillary flow assay device or system can have different shapes. For example, FIG. 3L shows an example where the sample retaining unit 306 is shaped differently (e.g., having a flat bottom).

Figure 4A:
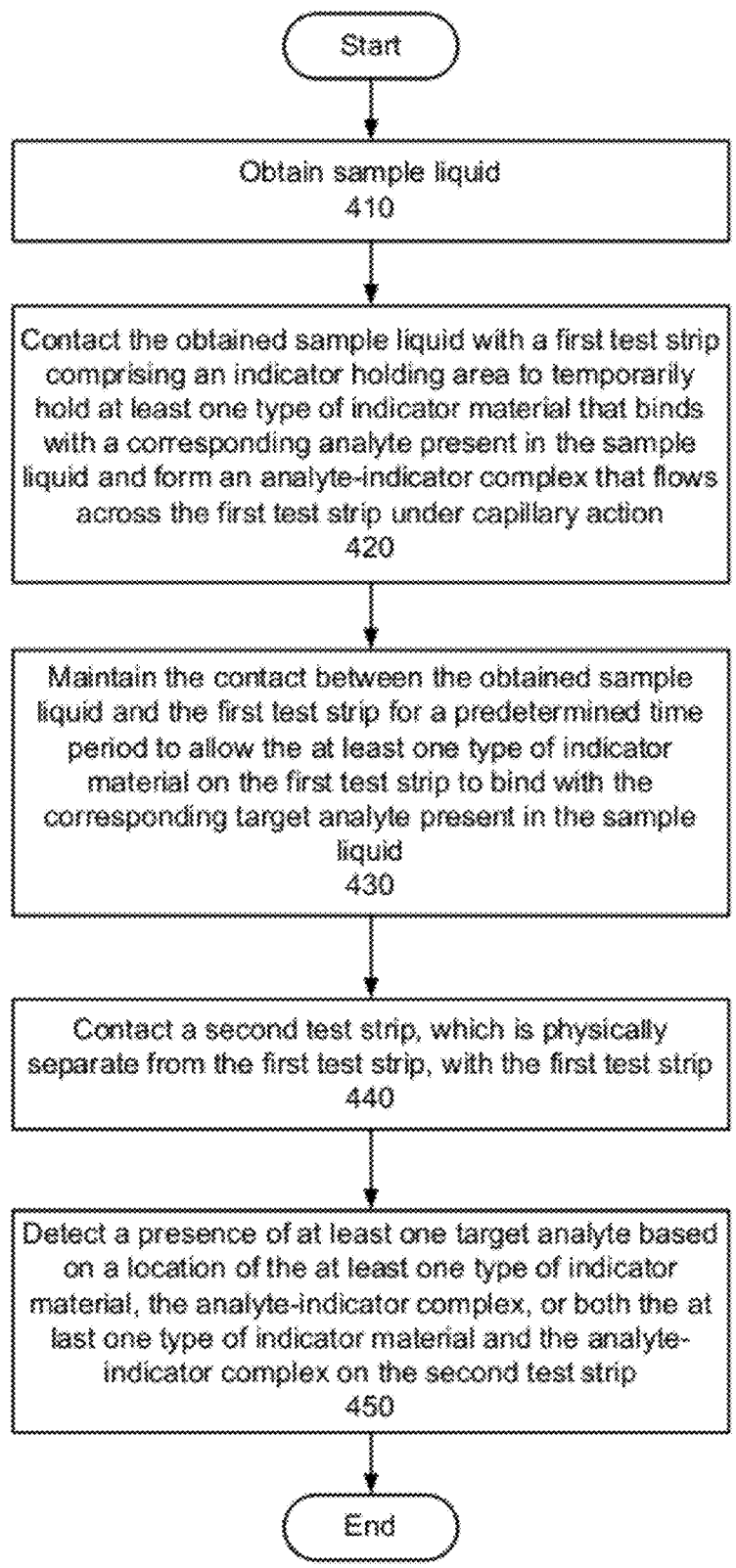
FIGS. 4A, 4B and 4C are process flow diagrams that show examples of processes for testing a sample liquid.
Figures 4B, 4C:
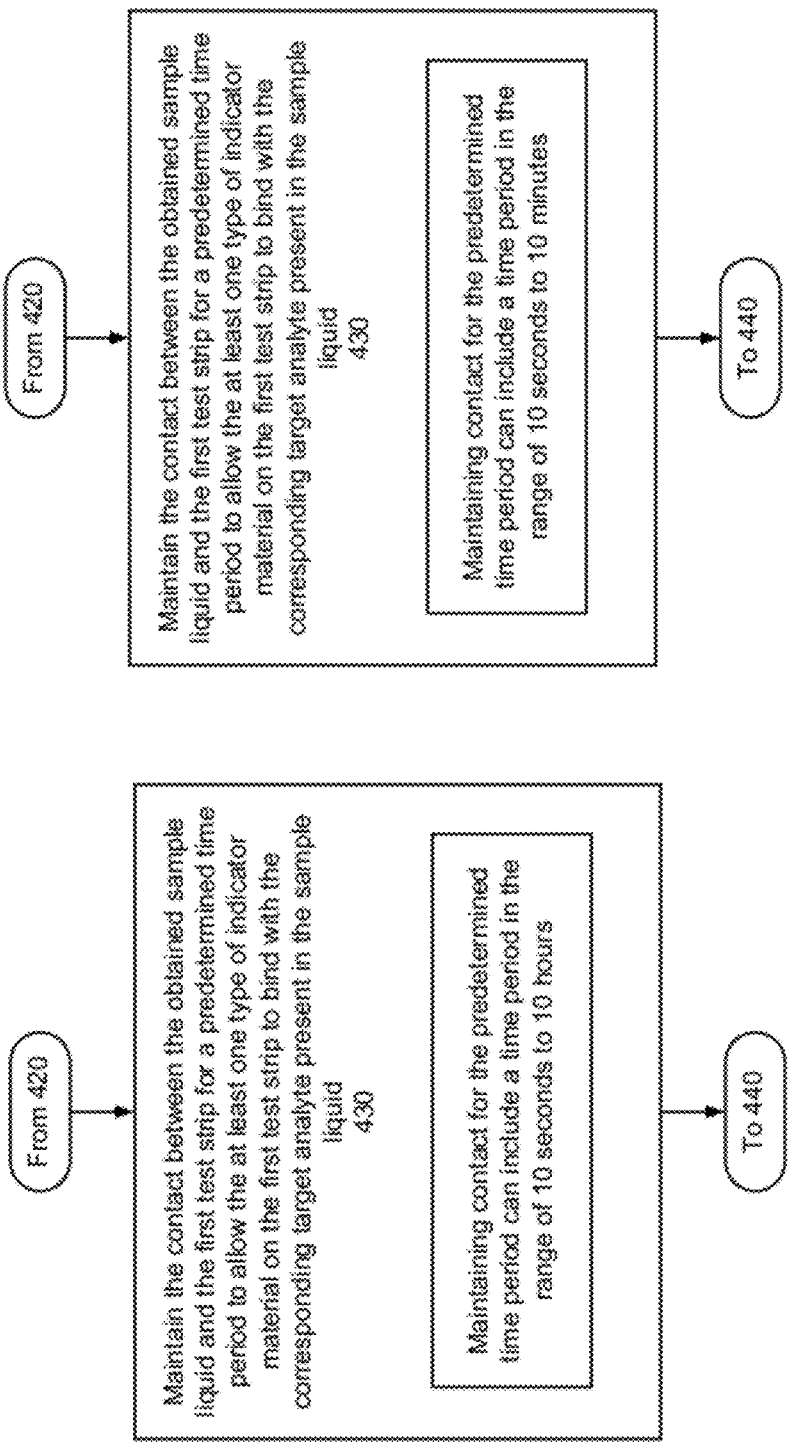

FIGS. 4A, 4B and 4C are process flow diagrams that show processes for testing a sample liquid using a testing unit that includes two separate pieces (e.g., discontinuous). A sample liquid is obtained (410). For example, the systems and devices described and shown in FIGS. 1A-3F and 3K can be used to obtain the sample liquid. The obtained sample liquid is contacted with a single united test strip or the first test strip comprising an indicator holding area to temporarily hold at least one type of indicator material that binds with a corresponding analyte present in the sample liquid and form an analyte-indicator complex that flows across the first test strip under capillary action (420). The first test strip can be implemented to be substantially the same as the first capillary flow support portion 110, the first piece or test strip 222 or the first piece or test strip of an assay device 312.

The contact between the obtained sample liquid and the first test strip can be maintained for a predetermined time period to allow the at least one type of indicator material on the first test strip to bind with the corresponding target analyte present in the sample liquid (430). As described above, an adequate binding time may be needed to allow a given analyte present in the sample liquid to bind with the indicator material. For example, the predetermined time period can include a time period in the range of 10 seconds to 10 hours (432).

Also, the predetermined time period can include a time period in the range of 10 seconds to 10 minutes (434). The predetermined time period to incubate the sample liquid with the indicator material can depend on the characteristics of the analytes present in the sample liquid.

A second test strip, which is physically separate from the first test strip, is put in contact with the first test strip (440). When the two test strips come into contact with one another, capillary flow resumes across the two test strips. The second test strip can include a binding area to immobilize a binder material configured to bind with the at least one type of indicator material, at least one analyte, or both the at least one analyte and the at least one type of indicator material. As described with respect to FIGS. 1A-1K, more than one binding area can be included with the second test strip.

A presence of at least one target analyte can be detected based on a location of the at least one type of indicator material, the analyte-indicator complex, or both the at last one type of indicator material and the analyte-indicator complex on the second test strip (450). For example, the presence of the visually detectably indicator material at the binding site can indicate that the sample liquid does not include a target analytes. Conversely, the presence of the visually detectable indicator material at the binding site can be used to indicate that a target analyte is present in the sample liquid. The use of the visual indicator can depend of the types of the indicator material, the types of the binder material, the types of the analyte or a combination therein.

Figure 5:
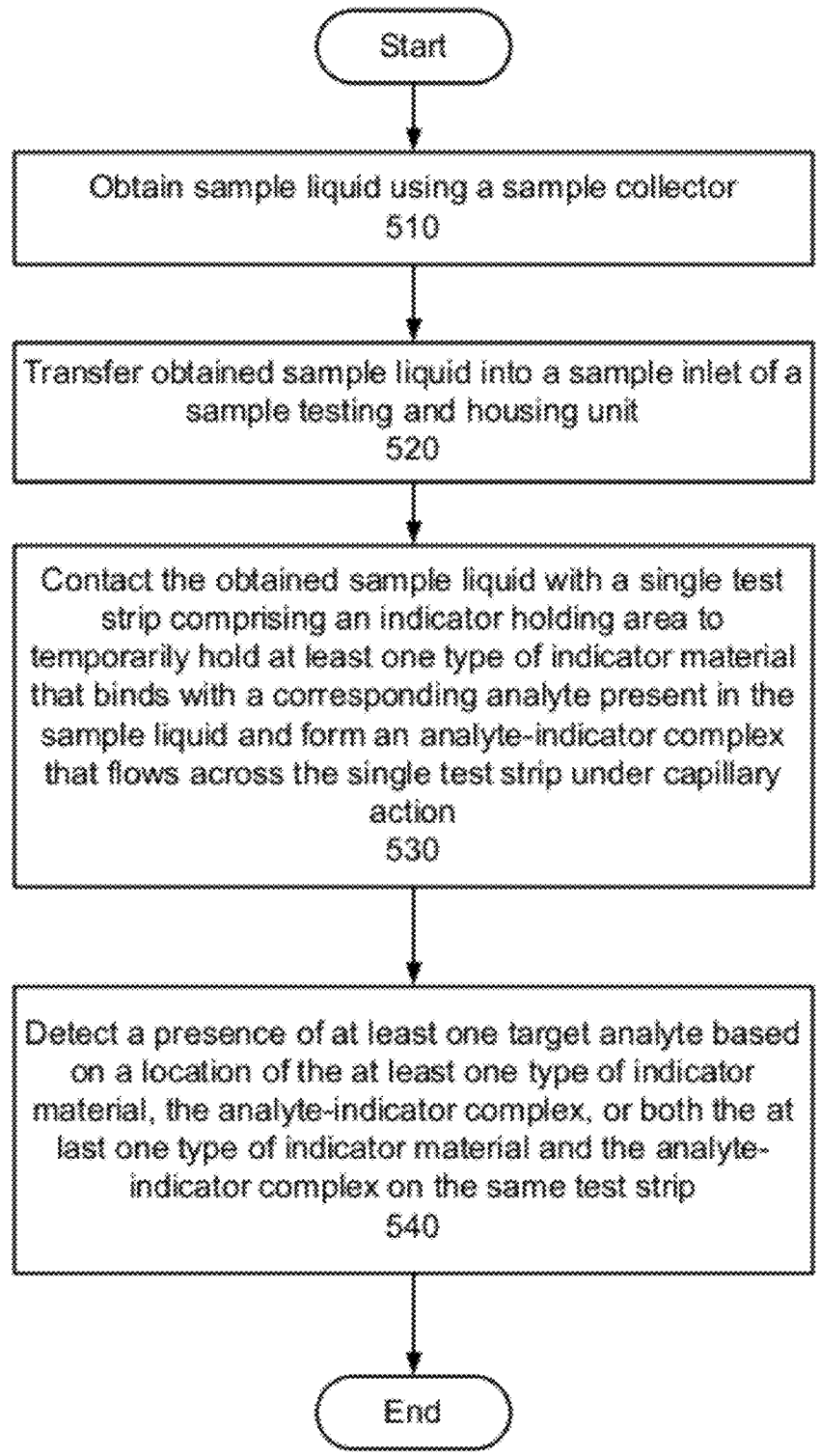
FIG. 5 shows an example process for using a capillary flow assay device or system to test a sample liquid.

FIG. 5 shows an example process for using a capillary flow assay device or system to test a sample liquid. A sample collector unit (e.g., sample collector unit 200) can be used to obtain a sample liquid (510). The obtained sample can be transferred into a sample inlet of a sample testing and housing unit (520). The obtained sample liquid can be contacted with a single test strip that includes an indicator holding area to temporarily hold at least one type of indicator material that binds with a corresponding analyte present in the sample liquid and form an analyte-indicator complex that flows across the single test strip under capillary action (530). The capillary action continues across the single test strip to a binding area that immobilizes a binder material configured to bind with the at least one type of indicator material, at least one analyte, or both the at least one analyte and the at least one type of indicator material. As described with respect to FIGS. 1A-1J, more than one binding area can be included with the second test strip. A presence of at least one target analyte can be detected based on a location of the at least one type of indicator material, the analyte-indicator complex, or both the at last one type of indicator material and the analyte-indicator complex on the same single test strip (540). For example, the presence of the visually detectably indicator material at the binding site can indicate that the sample liquid does not include a target analytes. Conversely, the presence of the visually detectable indicator material at the binding site can be used to indicate that a target analyte is present in the sample liquid. The use of the visual indicator can depend of the types of the indicator material, the types of the binder material, the types of the analyte or a combination therein.

The discontinuous (e.g., multiple piece test strip) and continuous (e.g., a single piece test strip) capillary flow assay devices described herein can be implemented to receive different test strips to test for various target analytes. The different test strips can be placed into the devices and removed one at a time, for example. Also, test strips that include different tracer materials can be used to test for multiple analytes at once. Additionally, several test strips can be placed together into the sample well to test for multiple analytes at once. The discontinuous capillary flow assay devices described herein can be used to test various liquid samples, such as saliva, urine or blood for drugs for example. In addition, dry samples can be placed in a solution and tested.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, the separation of various system components in the embodiments described above should not be understood as requiring such separation in all embodiments.

Only a few implementations and examples are described and other implementations, enhancements and variations can be made based on what is described and illustrated in this application.

What is claimed is:

1. A system for performing lateral capillary flow assay, comprising:
    a sample collection unit to collect a sample liquid; and
    a sample testing and storing unit to interface with the sample collection unit to test and store the collected sample liquid, the sample testing and storing unit comprising:
        a sample well to retain at least a portion of the sample liquid,
        a sample inlet positioned above the sample well and shaped to receive the collected sample liquid from the sample collection unit,
        a sample housing unit to store a remainder of the sample liquid not retained in the sample well, and
    an analyte testing unit housing shaped to receive an analyte testing unit to test a presence of a target analyte in the sample liquid, wherein the analyte testing unit housing comprises
        an analyte testing unit inlet positioned above the sample well to allow a first test strip to drop towards the sample well by gravity and into physical contact with the sample liquid in the sample well,
        a second test strip, physically separate from the first test strip, positioned within the sample well, the second test strip including a sample receiving area to receive the sample liquid,
    the second test strip comprising:
        an indicator holding area comprising at least one type of indicator material that binds with the target analyte in the sample liquid to form an analyte-indicator complex that flows across the analyte testing unit under capillary action, and the first test strip comprising:
        at least one binding area comprising at least one type of binder material configured to bind with the at least one type of indicator material, wherein a presence of the at least one type of indicator material at the at least one binding area indicates an absence of the target analyte, and a validation area comprising a ligand or the at least one type of binder material that selectively binds to the at least one type of indicator material to confirm that the at least one type of indicator material properly flowed across the analyte testing unit under capillary action.

2. The system of claim 1 wherein the at least one type of indicator material comprises a ligand and a label that can be measured or visualized based on color.

3. The system of claim 2, wherein the label comprises an agent selected from a group comprising a gold colloid, latex nanoparticles, iron nanoparticles, an enzyme, a fluorescent material, and a chemiluminescent material.

4. The system of claim 2, wherein the label is directly or indirectly linked to the ligand.

5. The system of claim 2 wherein the ligand comprises a chemical substance that selectively binds with the at least one analyte, the binder material or both the at least one analyte and the binder material.

6. The system of claim 2 wherein the at least one analyte comprises a chemical substance that selectively binds with the ligand, the binder material or both the ligand and the binder material.

7. The system of claim 2 wherein the binder material comprises a chemical substance that selectively binds with the ligand, the indicator material or both the ligand and the at least one type of indicator material.

8. The system of claim 1, comprising:
a filtering unit attached to an inner surface of the sample inlet to filter the sample liquid received from the sample collection unit.

9. The system of claim 1, further comprising:
a sample collector receiving unit positioned on a same side of the sample well as and parallel to the analyte testing unit housing such that the sample collection unit can be inserted into the sample collector receiving unit from above to cause the sample inlet to receive the collected sample.

10. The system of claim 1, wherein the first and the second test strips are positioned to allow the sample liquid to flow from the second test strip to the first test strip by capillary action.

* * * * *